US006291616B1

(12) United States Patent
Kiessling et al.

(10) Patent No.: US 6,291,616 B1
(45) Date of Patent: *Sep. 18, 2001

(54) METHODS AND REAGENTS FOR CAPPING RUTHENIUM OR OSMIUM CARBENE-CATALYZED ROMP PRODUCTS

(75) Inventors: Laura L. Kiessling, Madison, WI (US); Eva J. Gordon, Wheeling, IL (US); Laura E. Strong, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/336,121

(22) Filed: Jun. 17, 1999

(51) Int. Cl.[7] .............................. C08F 4/26; C08F 218/04
(52) U.S. Cl. .................. 526/171; 526/238.1; 526/238.2; 526/258; 526/266; 526/274; 526/281; 526/286; 526/297; 526/315; 526/316; 526/317.1; 526/332; 526/319
(58) Field of Search ..................................... 526/172, 281, 526/238.1, 238.2, 258, 266, 274, 286, 297, 315, 316, 317.1, 332, 319, 171

(56) References Cited

U.S. PATENT DOCUMENTS

| | | |
|---|---|---|
| 4,883,851 | 11/1989 | Grubbs et al. . |
| 5,100,972 | 3/1992 | Sivavec et al. . |
| 5,312,940 | 5/1994 | Grubbs et al. . |
| 5,342,909 | 8/1994 | Grubbs et al. . |
| 5,587,442 | 12/1996 | Kiessling et al. . |
| 5,710,298 | 1/1998 | Grubbs et al. . |
| 5,750,815 | 5/1998 | Grubbs et al. . |
| 5,831,108 | 11/1998 | Grubbs et al. . |
| 5,849,851 | 12/1998 | Grubbs et al. . |
| 5,880,231 * | 3/1999 | Grubbs et al. .................. 526/171 |
| 5,889,128 | 3/1999 | Schrock et al. . |

OTHER PUBLICATIONS

NIH Grant Abstract No. 5R01GM55984–03 entitled "Multivalent Protein Carbohydrate Interactions" Jun. 1, 1997.

D. Albagli et al., "New Functional Polymers Prepared by Ring–Opening Metathesis Polymerization: Study of the Quenching of Luminescence of Pyrene End Groups by Ferrocene or Phenothiazine Centers in the Polymers," *J. Phys. Chem.*, 10211–10216 (1993).

D.Abagli et al., "Surface Attachment of Well–Defined Redox–Active Polymers and Block Polymers via Terminal Functional Groups," *J. Am. Chem. Soc.*, 115:7328–7334 (1993).

Biagini et al., "Synthesis of Penicillin Derived Polymers Utilizing Ring–Opening Metathesis Polymerization Methodology," *Chem. Commun.*, 1097–1098 (1997).

Biagini et al., "Living Ring–Opening Metathesis Polymerization of Amino Ester Functionalized Norbornenes," *Polymer*, 39: 1007–1014 (1998).

M. Buerke et al., "Sialyl Lewis*–containing Oligosaccharide Attenuates Myocardial Reperfusion Injury in Cats," *J. Clin. Invest.*93: 1140–1148 (1994).

(List continued on next page.)

*Primary Examiner*—David W. Wu
*Assistant Examiner*—R. Harlan
(74) *Attorney, Agent, or Firm*—Greenlee, Winner and Sullivan, P.C.

(57) ABSTRACT

Methods of preparing a telechelic polymer (mono- or bi-telechelic) that use a ruthenium or osmium carbene catalyst and a capping agent, at least one of which is functionalized.

48 Claims, 8 Drawing Sheets

OTHER PUBLICATIONS

L. F. Cannizzo et al., "End Capping Polynorbornene Produced by Titanacyclobutanes," *Macromolecules*, 20: 1488–1490 (1987).

A. Y. Chernayk et al., "Synthesis of Lysine–Containing Fragments of the *Proteus Mirabilis* O27 O–Specific Polysaccharide and Neoglyco–conjugates Therefrom," *Carbohyd. Res.*, 225: 279–289 (1992).

I. del Rio et al., "Ring–Opening Metathesis Polymerization of Norbornene Catalyzed by a Ru(II)–Vinylidene Complex," *Tetrahedron Lett.*, 40: 1401–1404 (1999).

E. L. Dias et al., "Well–Defined Ruthenium Olefin Metathesis Catalyst: Mechanism and Activity," *J. Am. Chem. Soc.*, 119: 3887–3897 (1997).

E. L. Dias et al., "Synthesis and Investigation of Homo– and Heterobimetallic Ruthenium Olefin Metathesis Catalysts Exhibiting Increased Activities," *Oragnometallics*, 17: 2758–2767 (1998).

A. Furstner et al., "A Most User–Friendly Protocol for Ring Closing Metathesis Reactions," *Chem. Commun.*, 95–96 (1999).

V. C. Gibson et al., "Thymine Functionalized Polymers Via Living Ring–Opening Metathesis Polymerization," *Chem. Commun.*, 1095–1096 (1997).

Goldstein et al., Chapter 4, "Carbohydrate Binding Specificity of Concanavalin A" in Concanavalin A as A Tool; H. Bittiger and H. P. Schnebli, Ed., John Wiley & Sons, Ltd.: London, 1976; Coll., pp. 55–65.

E. J. Gordon et al., "Glycoprotein–Inspired Materials Promote the Proteolytic Release of Cell Surface L–Selectin," *Bioorg. Med. Chem.*, 6: 1293–1299 (1998).

E. J. Gordon et al., "Synthetic Ligands Point to Cell Surface Strategies," *Nature*, 392: 30–31 (1998).

R. H. Grubbs, "The Development of Functional Group Romp Tolerant Catalysts," *J.M.S. Pure Appl. Chem.*, A31: 1829–1833 (1994).

M. A. Hillmyer et al., "Ring–Opening Metathesis Polymerization of Functionalized Cyclooctenes by a Ruthenium–Based Metathesis Catalyst," *Macromolecules* 28: 6311–6316 (1995).

K. J. Ivin et al., Chapter 11, "Ring–Opening Metathesis Polymerization: General Aspects," *Olefin Metathesis and Metathesis Polymerization*; Academic Press: San Diego, CA, pp. 224–259 (1997).

M. Kanai et al., "Varying the Size of Multivalent Ligands: The Dependence of Concanavalin A Binding on Neoglycopolymer Length," *J. Am. Chem. Soc.*, 119: 9931–9932 (1997).

L. L. Kiessling et al., "Bioactive Polymers," Topics in Organometallic Chemistry, vol. 1: *Alkene Metathesis in Organic Synthesis* A. Furstner. Ed. Springer (1998) pp. 199–231.

J. E. Kingery–Wood et al., "The Agglutination of Erythrocytes by Influenza Virus is Strongly Inhibited by Liposomes Incorporating an Analog of Sialyl Gangliosides," *J. Am. Chem. Soc.*, 114: 7303–7305 (1992).

J. S. Kingsbury et al., "A Recyclable Ru–Based Metathesis Catalyst," *J. Am. Chem. Soc.*, 121: 791–799 (1999).

R. T. Lee et al., "Synthesis of 3–(2–Aminoethylthio)Propyl Glycosides," *Carbohyd. Res.*, 37: 193–201 (1974).

D. M. Lynn et al., "Living Ring–Opening Metathesis Polymerization in Aqueous Media Catalyzed by Well–Defined Ruthenium Carbene Complexes," *J. Am. Chem. Soc.*, 118: 784–790 (1996).

D. M. Mann et al., "Probing Low Affinity and Multivalent Interactions with Surface Plasmon Resonance: Ligands for Concanavalin A," *J. Am. Chem. Soc.*, 120: 10582 (1998).

D. D. Manning et al., "Neoglocopolymer Inhibitors of the Selectins," *Tetrahedron*, 53: 11937–11952 (1997).

K. H. Mortell et al., "Recognition Specificity of Neoglycopolymers Prepared by Ring–Opening Metathesis Polymerization," *J. Am. Chem. Soc.*, 118: 2297–2298 (1996).

K. H. Mortell et al., "Synthesis of Cell Agglutination Ihhibitors by Aqueous Ring–Opening Metathesis Polymerization," *J. Am. Chem. Soc.*, 116: 12053–12054 (1994).

T. Osawa et al., "Gorse (*Ulex europeus*) Phytohemagglutinins," *Methods Enzymol.*, 28: 323–327 (1972).

R. Roy et al. "Custom–Designed Glocopolymer Syntheses by Terpolymerizations," *J. Chem. Soc., Chem. Commun.*, No. 21, 1611–1613 (1992).

R. Roy et al., "Solid–Phase Synthesis of Dendritic Sialoside Inhibitors of Influenza A Virus Haemagglutinin," *J. Chem. Soc., Chem. Commun.*, 1869–1872 (1993).

W. J. Sanders et al., "Inhibition of L–Selectin–Mediated Leukocyte Rolling by Synthetic Glycoprotein Mimics," *J. Biol. Chem.*, 274: 5271–5278 (1999).

R. L. Schnaar et al., "Preparation of Polyacrylamide Gels Containing Active Esters," *Methods in Enzymology*, 83: 306–310 (1982).

M. Scholl et al., "Increased Ring Closing Metathesis Activity of Ruthenium–Based Olefin Metathesis Catalysts Coordinated with Imidazolin–2–ylindene Ligands," *Tetrahedron Lett.*, 40: 2247–2250 (1999).

R. R. Schrock et al., "Synthesis of Molybdenum Imido Alkylidene Complexes and Some Reactions Involving Acyclic Olefins," *J. Am. Chem. Soc.*, 112: 3875–3886 (1990).

P. Schwab et al., "Synthesis and Applications $RuCl_2(=CHR')(PR_c)_2$ : The Influence of the Alkylidene Moiety on Metathesis Activity," *J. Am. Chem. Soc,*, 118: 100–110 (1996).

P. Schwab et al., "A Series of Well–Defined Metathesis Catalysta– Synthesis of $[RuCl_2(=CHR')(PR_3)_2]$ and Its Reactions," *Angew, Chem. Int. Ed. Engl.*, 34: 2039–2041 (1995).

A. Spaltenstein et al., "Polyacrylamides Bearing Pendant – Sialoside Groups Strongly Inhibit Agglutination of Erythrocytes by Influenza Virus," *J. Am. Chem. Soc.*, 113: 687–688 (1991).

M. A. Sparks et al., "Neuraminidase–Resistant Hemagglutination Inhibitors: Acrylamide Copolymers Containing a C–Glycoside of N–Acetylneuraminic Acid," *J. Med. Chem.*, 36: 778–783 (1993).

W. Spevak et al., "Polymerized Liposomes Containing C–Glycosides of Sialic Acid: Potent of Influenza Virus in Virto Infectivity," *J. Am. Chem. Soc.*, 115: 1146–1147 (1993).

W. C. Still, "Rapid Chromotographic Technique for Preparative Separations with Moderate Resolution," *J. Org. Chem.*, 43: 2923–2925 (1978).

A Varki, "Selectin Ligands," *Proc. Natl. Acad. Sci, USA*, 91: 7390–7397 (1994).

C. D. Ver Nooy et al., "Formation of Nortricyclene Derivatives by Bromination of $_{exo}$–2,5–Methylene–1,2,5,6–tetrahydrobenzoic Acids," *J. Am. Chem. Soc.*, 77: 3583–3586 (1955).

M. Weck et al., "Ring–Opening Metathesis Polymerization from Surfaces," *J. Am. Chem. Soc.*, 121: 4088–4089 (1999).

T. Weskamp et al., "A Novel Class of Ruthenium Catalysts for Olefin Metathesis," *Angew, Chem., Int. Ed. Engl.*, 37: 2490–2493 (1998).

\* cited by examiner metal chelators protein recognition domains solid supports

= Wang resin (a polystyrene base matrix)

Fig. 8A
Fig. 8B
Fig. 8C
FITC-anti-CD62L Antibody
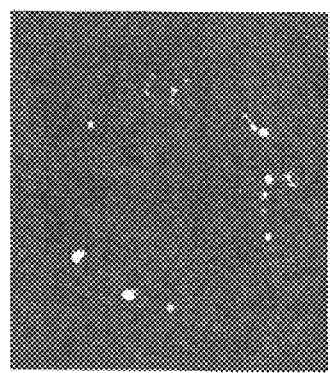
FITC-neoglycopolymer
(hydrazone)
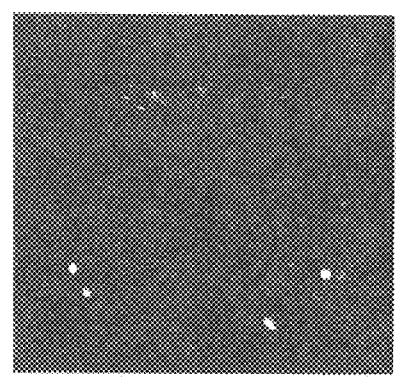
FITC-neoglycopolymer
(TEG-amide)

METHODS AND REAGENTS FOR CAPPING RUTHENIUM OR OSMIUM CARBENE-CATALYZED ROMP PRODUCTS

STATEMENT OF GOVERNMENT RIGHTS

The present invention was made with the support of the National Institutes of Health Grant No. GM-55984. The government may have certain rights in the invention.

BACKGROUND

New materials and methods of synthesis are emerging as significant areas of research and manufacturing. They have applications in the fields of biotechnology, medicine, pharmaceuticals, medical devices, sensors, optical materials, etc. The ring-opening metathesis polymerization (ROMP) method has emerged as a powerful synthetic method for the creation of such useful materials. Many examples in which ROMP has been used to generate functionalized materials have focused on the incorporation of pendant functionality into the monomers, thereby forming a multivalent array. As used herein, a multivalent array refers to a polymer (random or blocks of varying lengths, including shorter oligomers) having pendant functional groups that impart various properties to the polymer. Such multivalent arrays are also often referred to as multivalent ligands, multivalent displays, multidentate arrays, multidentate ligands, or multidentate displays.

Such multivalent arrays are particularly useful in the medical and biotechnology areas. For example, the binding of cell surface receptors to particular epitopes of multivalent arrays can trigger a wide variety of biological responses. Such multivalent binding events have unique consequences that are dramatically different than those elicited by monovalent interactions. For instance, signaling through the epidermal growth factor is promoted by the binding of divalent ligands, which apparently promote dimerization of the transmembrane receptor, yet monovalent ligands also bind the receptor but produce no signal. In addition, multivalent arrays have been shown to induce the release of a cell surface protein, suggesting a new mechanism for controlling protein display. In protein-carbohydrate recognition processes, multivalent saccharide-substituted arrays can exhibit increased avidity, specificity, and unique inhibitory potencies under dynamic conditions of shear flow. Thus, the ability to synthesize defined, multivalent arrays of biologically relevant binding epitopes provides a means for exploring and manipulating physiologically significant processes.

One way in which this could be done is through the use of ROMP technology. ROMP has been used to generate defined, biologically active polymers (Gibson et al., *Chem. Commun.*, 1095–1096 (1997); Biagini et al., *Chem. Commun.*, 1097–1098 (1997); Biagini et al., *Polymer*, 39, 1007–1014 (1998); and Kiessling et al., *Topics in Organometallic Chemistry*, 1, 199–231 (1998)) with potent and unique activities that range from inhibiting protein-carbohydrate recognition events to promoting the proteolytic release of cell surface proteins (Mortell et al., *J. Am. Chem. Soc.*, 118, 2297–2298 (1996); Mortell et al., *J. Am. Chem. Soc.*, 116, 12053–12054 (1994); Kanai et al., *J. Am. Chem. Soc.*, 119, 9931–9932 (1997)); Kingsbury et al., *J. Am. Chem. Soc.*, 121, 791–799 (1999); Schrock et al., *J. Am. Chem. Soc.*, 112, 3875–3886 (1990); Gordon et al., *Nature*, 392, 30–31 (1998); and Sanders et al., *J. Biol. Chem.*, 274, 5271–5278 (1999). The assembly of multivalent materials by ROMP has several advantages over classical methods for generation of multivalent displays. Specifically, ROMP can be performed under living polymerization conditions, and if the rate of initiation is faster than that of propagation, varying the monomer to initiator ratio (M:I) can generate materials of defined length (Ivin, Olefin Metathesis and metathesis polymerization; Academic Press: San Diego, 1997). This approach has been successfully applied with the Grubb's ruthenium metal carbene catalyst ($[(Cy)_3P]_2Cl_2Ru$=CHPh) to generate materials with narrow polydispersities, indicating that the resulting substances are fairly homogeneous (Dias et al., *J. Am. Chem. Soc.*, 119, 3887–3897 (1997); and Lynn et al., *J. Am. Chem. Soc.*, 118, 784–790 (1996)). In contrast to anionic and cationic polymerization catalysts, ruthenium metal carbene initiators are tolerant of a wide range of functional groups.

An additional strategy for further modification is to incorporate selected functional groups at the termini. The attachment of additional functionality at polymer termini further expands the repertoire of uses for materials generated by ROMP. This selective end-capping has been used previously in living titanium and molybdenum-initiated ROMP reactions to synthesize materials for new applications, as demonstrated in the synthesis of surfaces bearing ROMP-derived polymers (Cannizzo et al., *Macromolecules*, 20, 1488–1490 (1987); Albagli et al., *J. Phys. Chem.*, 97, 10211–10216 (1993); and Albagli et al., *J. Am. Chem. Soc.*, 115, 7328–7334 (1993)). Unlike the titanium and molybdenum initiators, ruthenium ROMP initiators are tolerant of a wide variety of polar functional groups, allowing generation of products not accessible using other catalysts (Grubbs, *J.M.S. Pure Appl Chem.*, A31, 1829–1833 (1994). The attachment of specific end groups to polymers generated by ruthenium carbene-catalyzed ROMP would provide access to materials amenable to further functionalization for applications such as selective immobilization of polymers to create new surfaces (Weck et al., *J. Am. Chem. Soc.*, 121, 4088–4089 (1999)) and the development of specific ligands that report on binding events, for example. Thus, what is needed are methods and reagents for the incorporation of selected functionality into the terminii of polymers generated by ruthenium carbene-catalyzed ROMP.

SUMMARY

The present invention provides methods and reagents for the terminal attachment of functional groups to materials generated by ROMP. These methods and reagents can be used to synthesize a variety of functionalized polymers (herein, included within this term are relatively short oligomers). Significantly, the methods of the present invention can provide access to a wide range of materials with significant functions. For example, they can be used to generate libraries of oligomeric substances that differ in terminal functionality as well as in length. Such materials can include functionality that allows for immobilization on a substrate surface, for example. Alternatively, such materials can include reporter groups such as functionality capable of fluorescence, which allows for the creation of a molecular probe that can be used to visualize a receptor-ligand interaction on a cell surface. Another advantage of incorporating terminal functionality is that this can allow for easier purification of the polymers. Such diverse materials can be prepared using a capping agent, preferably a bifunctional capping agent, and/or a functionalized metathesis catalyst.

In one embodiment of the present invention a method of preparing a telechelic polymer (preferably, a monotelechelic polymer) is provided. The method includes: polymerizing at least one monomer comprising at least one polymerizable group in the presence of at least one ruthenium or osmium carbene catalyst to form a polymer template; and combining the polymer template with at least one functionalized capping agent under conditions effective to react the polymer template with the capping agent to form a terminally functionalized polymer.

The functionalized capping agent can include a latent reactive group for subsequent reaction with a functionalizing reagent. Alternatively, the functionalized capping agent can include a nonreactive functional group (i.e., one that has the desired functionality without further reaction).

In another embodiment, the present invention provides a method of preparing a telechelic polymer that involves: polymerizing at least one monomer comprising at least one polymerizable group in the presence of at least one functionalized ruthenium or osmium carbene catalyst to form a functionalized polymer template; and combining the functionalized polymer template with at least one capping agent under conditions effective to react the functionalized polymer template with the capping agent to form a terminally functionalized polymer.

The functionalized carbene catalyst can include a latent reactive group for subsequent reaction with a functionalizing reagent. Alternatively, the functionalized carbene catalyst can include a nonreactive functional group (i.e., one that has the desired functionality without further reaction).

In yet another embodiment, the present invention provides a method of preparing a bitelechelic polymer. The method involves: polymerizing at least one monomer comprising at least one polymerizable group in the presence of at least one functionalized ruthenium or osmium carbene catalyst to form a functionalized polymer template; and combining the functionalized polymer template with at least one functionalized capping agent under conditions effective to react the functionalized polymer template with the capping agent to form a bitelechelic polymer.

Also provided is a functionalized capping agent and a functionalized carbene.

BRIEF DESCRIPTION OF THE DRAWINGS

FIG. 8. Fluorescein-labeled anti-L-selectin antibody (A), fluorescein-conjugated neoglycopolymer 12(B), and fluorescein-conjugated neoglycopolymer 17(C) binding to Jurkat cells as observed by fluorescence microscopy. Each image is an individual cell at 630× magnification and is representative of at least four independent experiments.

DETAILED DESCRIPTION OF PREFERRED EMBODIMENTS

The present invention provides methods and reagents for the terminal attachment of new functional groups to materials generated by ROMP. Preferred embodiments of the methods of the present invention are significant because they are relatively high yielding, general, convenient, and/or efficient for the preparation of polymers of varying average lengths and varying terminal functionality, for example. Significantly, the attachment of chain terminating functionality to polymers generated by metal carbene-catalyzed ROMP provides access to a wider variety of materials than previous polymerization methods were able to provide. Such materials may provide unique surfaces or ligands for a wide variety of natural and synthetic receptors.

Figure 1:
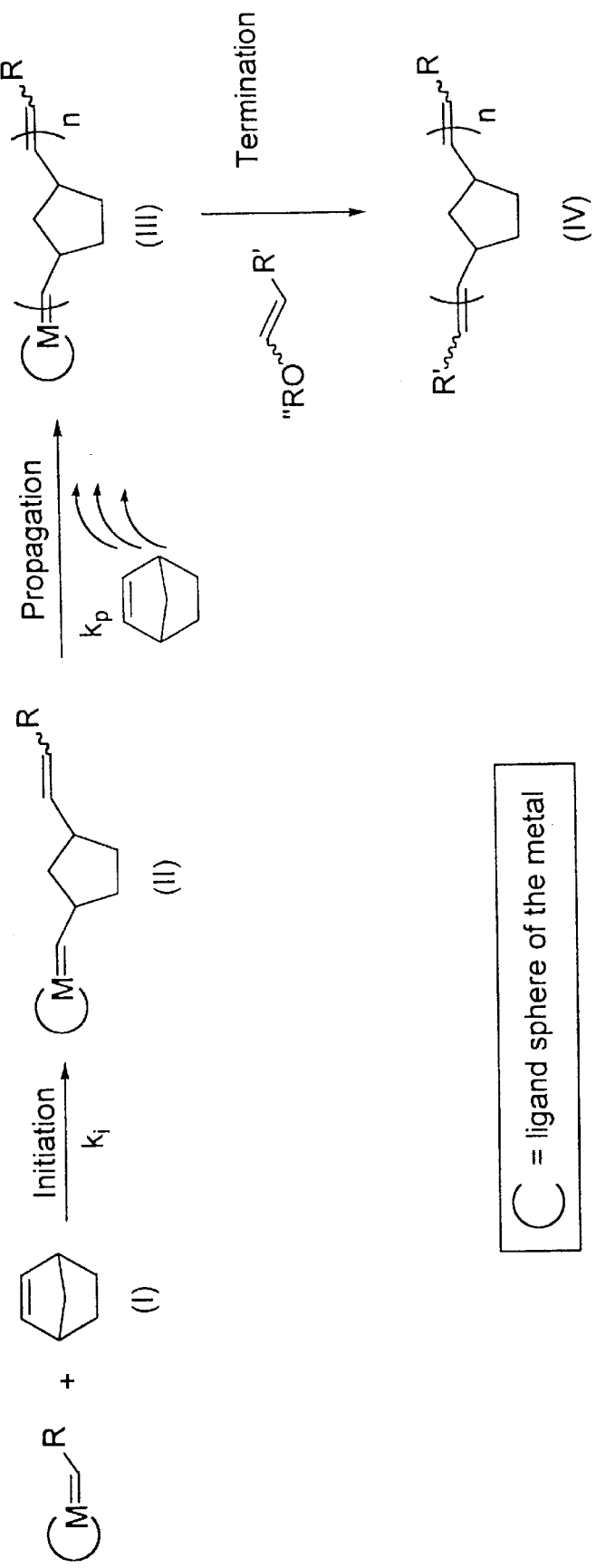
FIG. 1. Mechanism and intermediates in ring-opening metathesis polymerization (ROMP) demonstrating the incorporation of a functional group in the carbene catalyst and termination with a derivatized electron rich olefin.

The methods of the present invention are based on the living polymerization of a monomer by a ruthenium or osmium carbene-catalyzed ROMP system. In preferred methods, the rates of termination and chain transfer are relatively slow compared to propagation. When initiation ($k_i$) is fast relative to propagation ($k_p$) such that $k_i > k_p$, homogeneous materials of controlled lengths and low polydispersities can be generated (FIG. 1). In a living polymerization, the active metal carbene center is present at the end of each chain after the monomer is consumed (FIG. 1, III). This species can react with electron-rich alkenes to yield a product with a terminal alkene (IV), which can be functionalized, and an unreactive alkoxy-substituted ruthenium metal carbene. A significant advantage to this strategy is that only living chains can acquire the functionality, resulting in a more homogeneous population of functionalized materials.

Figure 2:
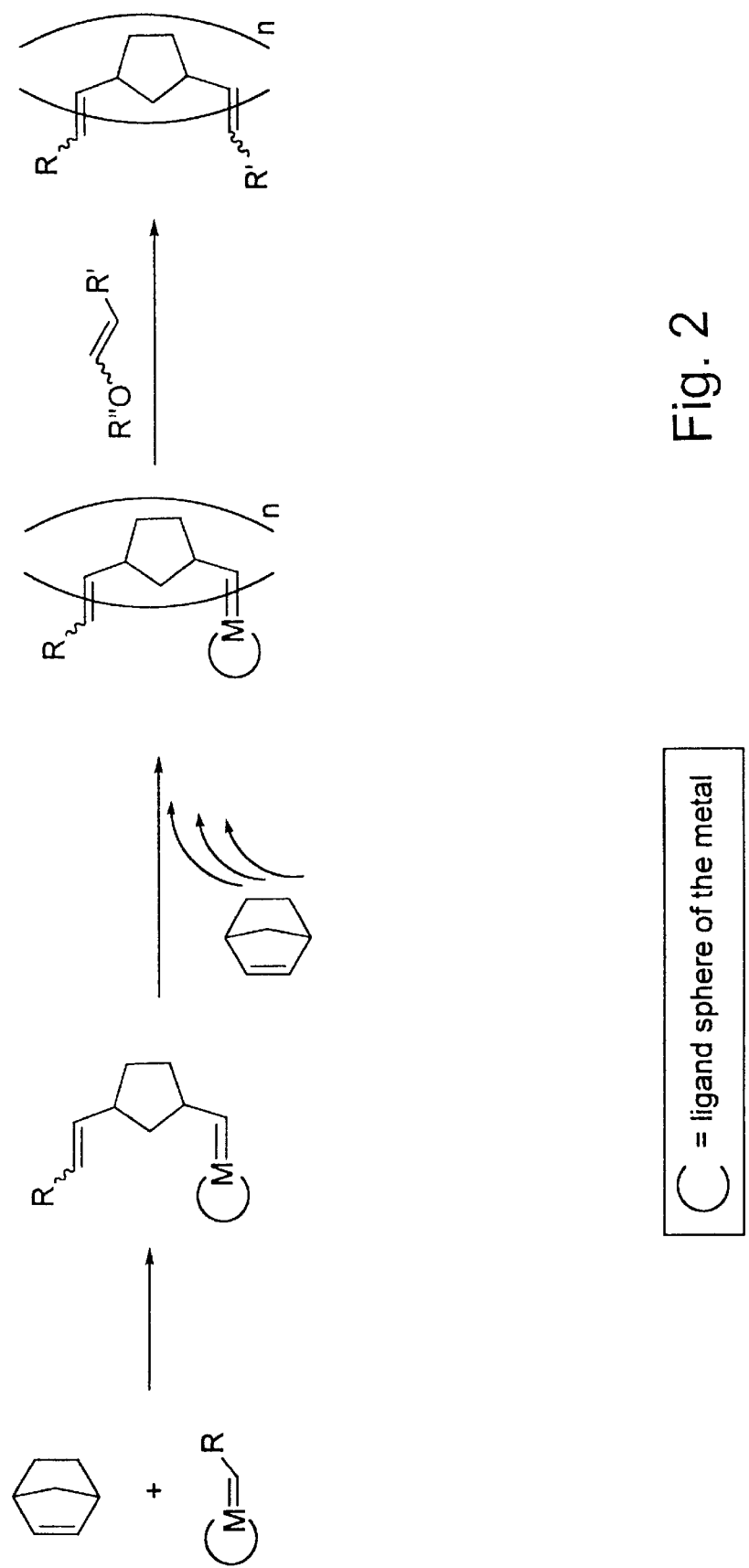
FIG. 2. Mechanism and intermediates in ring-opening metathesis polymerization (ROMP) of monotelechelic (if either R or R' includes functionality) and bitelechelic polymers (if both R and R' include functionality).

As shown in FIG. 2, this strategy generates telechelic polymers, i.e., a polymer that contains one or more end groups with unique functionality. This approach has a distinct advantage over previous methods because the length of each polymer block can be controlled. Telechelic polymers can have one or more unique end groups and in this method these would be accessible. Referring to FIG. 2, monotelechelic polymers are those products in which either R or R' includes functionality, whereas bitelechelic polymers are those products in which both R and R' include functionality. For example, monofunctional polymers can be the result of using a functionalized capping agent or a functionalized catalyst, as described in greater detail below. In turn, the bitelechelic polymers can be created when both a functionalized catalyst and a functionalized capping agent are used. In addition to the biological examples enclosed, telechelic polymers are often used in the synthesis of crosslinked plastics. Enhancement of desired properties, such as thermal stability, may result from the ability to generate defined, homogeneous materials.

The method involves either conventional ROMP methodology or the improved methodology of Applicants' Assignee's copending U.S. patent application Ser. No. 09/335,430, filed on even date herewith, entitled "Methods for Making Multivalent Arrays." Briefly, in conventional ROMP polymerization methods, a monomer is used to make a polymer that includes the desired pendant functional groups, whereas in the improved method, the desired pendant functional groups are attached to preformed polymers that include latent reactive groups.

In the latter (improved) method, a monomer is used that includes in its structure at least one polymerizable group and at least one latent reactive group for subsequent attachment of a pendant functional group (i.e., subsequent functionalization). Thus, suitable latent reactive groups are those that are unreactive during the initial ROMP reaction. Examples of monomer latent reactive groups include activated leaving groups such as an activated ester or protected functional groups such as a protected amine. As used herein, a "protected" group is one in which the intrinsic reactivity of the group is masked temporarily (i.e., the "mask" can be removed). incorporated from U.S. patent application Ser. No. 09/335,430, filed Jun. 17, 1999:

Latent reactive groups on the monomers that are used for functionalization include electrophilic or nucleophilic groups. Analogously, the compounds from which the pendant functional groups are derived (i.e., the fuctionalizing reagents) include electrophilic or nucleophilic groups. These two sets of groups may be the same or different, although for any two reactants (monomer and functionalizing reagent) the latent reactive groups are matched to allow for reaction and attachment of the pendant functional group to the polymer template. The resultant polymer acts as a template to which one or more functional groups can be appended using one or more functionalizing reagents that react with the latent reactive groups derived from the monomers (herein referred to as monomer latent reactive groups). These functional groups may provide a recognition element (i.e., binding site) for a biological entity, such as a cell surface receptor. Alternatively, they may be generally unreactive (e.g., nonbinding to a cell surface receptor). Thus, the resultant polymers may be bioactive or biocompatible.

Examples of suitable monomers are disclosed, for example, in various documents cited in the Background Section, as well as U.S. Pat. Nos. 5,831,108, 5,342,909, 5,710,298, 5,312,940, 5,750,815, 5,880,231, 5,849,851, 4,883,851, and 5,587,442. Preferred monomers having latent reactive groups are disclosed in Applicants' Assignees copending U.S. patent application Ser. No. 09/335,430, filed on even date herewith, entitled "Methods for Making Multivalent Arrays." Such monomers may be used alone or with prefunctionalized monomers (i.e., those having pendant groups that do not require further functionalization).

Suitable monomers for use in the methods of the present invention, having at least one polymerizable group (and often only one polymerizable group) and at least one latent reactive group (used for functionalization), that can be used to make a polymer template are those that are stable to the ROMP polymerization conditions. Preferably, suitable monomers are those that can be polymerized through ROMP under standard conditions. More preferably, the monomers include substituted cyclic (e.g., monocyclic, bicyclic, tricyclic, or higher order cyclics) mono-olefins. Examples include, but are not limited to, strained olefins such as norbornene, cyclobutene, and less strained olefins such as cyclooctene. Such substituted cyclic mono-olefins can also include heteroatoms and functional groups within the ring, including, for example, thioethers (RSR' or $R_2S$), ethers (ROR' or $R_2O$), amines (primary RNH2; secondary RR"NH or $R_2NH$; tertiary RR'R"N or $R_2R'N$ or $R_3N$), amides (i.e. RCONHR'), and esters ($RCO_2R'$). Examples of such olefins include oxanorbornene, 7-thia-bicyclo[2.2.1]hept-2-ene, and 3,6,7,8-tetrahydro-1H-azocin-2-one, the structures of which are as follows:

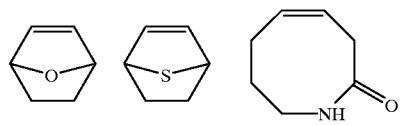

An example of a class of suitable monomers based on the norbornene ring structure has the following general structure:

I,

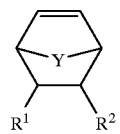

Formula I wherein Y is $CH_2$, O, S, or N—$R^3$ (wherein $R^3$ is H or an organic group), $R^1$ and $R^2$ may be H or an organic group, which may be connected such that they form a ring, with the proviso that at least one of $R^1$ and $R^2$ includes a latent reactive group as defined in Applicants' Assignee's copending U.S. patent application Ser. No. 09/335,430, filed on even date herewith, entitled "Methods for Making Multivalent Arrays," such as an activated ester. A specific example is bicyclo [2.2.1]hept-5-ene-exo-2-carboxylic acid N-hydroxysuccinimide ester.

Thus, the monomers that can be polymerized to form polymers that are subsequently functionalized at their terminii according to the methods of the present invention can include a variety of functionality such as: (1) monomer latent reactive groups that can be functionalized to include pendant functional groups after polymerization; (2) nonreactive functionality that does not require further functionalization to produce the desired pendant functional groups (which can be simple or complex); or (3) no pendant functional groups (as in norbornene). Various combinations of such monomers can be used in the methods of the present invention to provide block or random copolymers.

Figure 3:
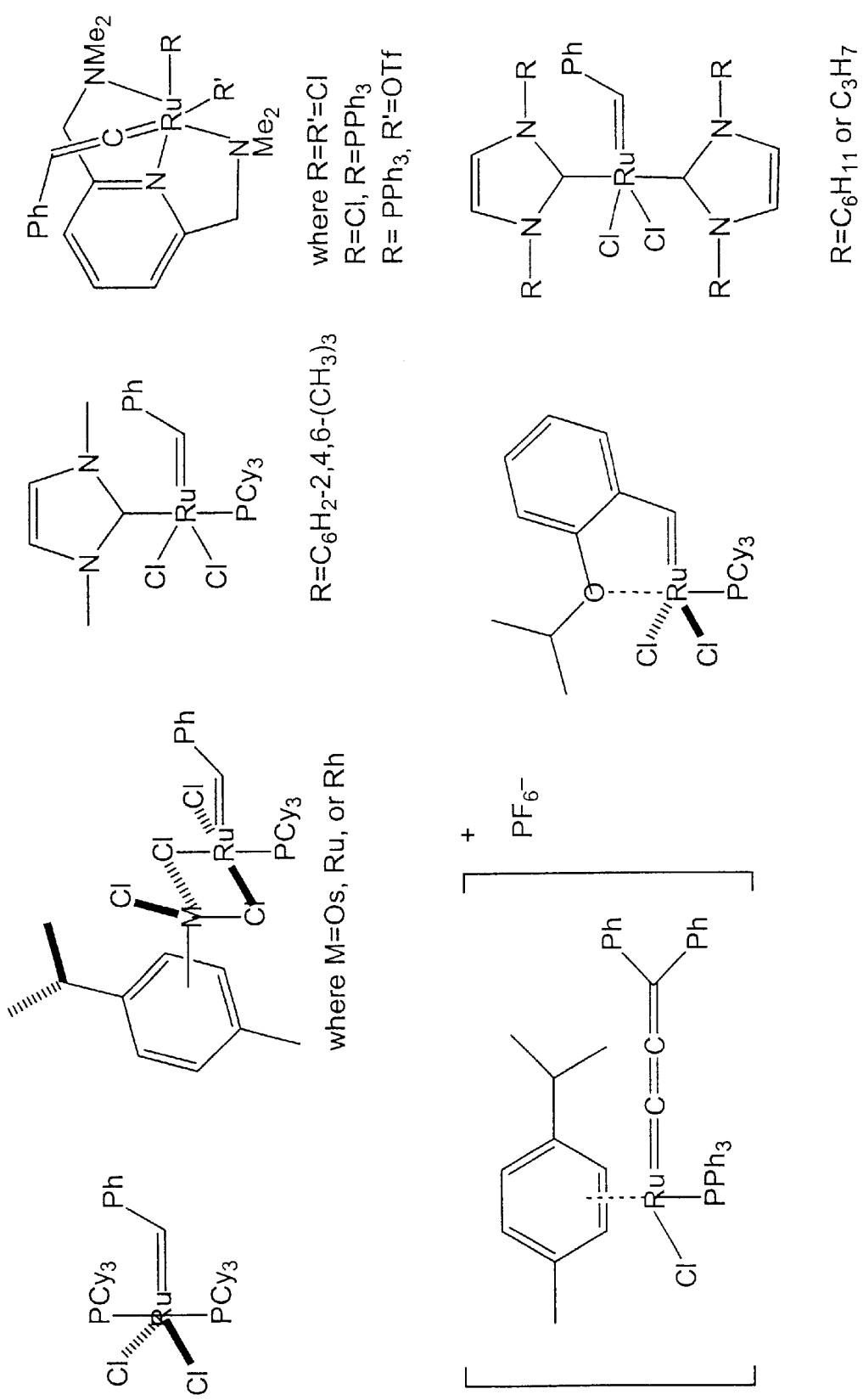
FIG. 3. Examples of metal carbene catalysts suitable for use in the present invention.

In either ROMP reaction (conventional or improved), varying the ratio of monomer to ROMP catalyst (i.e., initiator) results in varying the length of the resultant polymer. The polymer (or polymer template) is preferably prepared by polymerizing one or more monomers using a metal carbene catalyst (i.e., a compound containing a metal carbene (M=$CR^4R^5$) bond that catalyzes metathesis reactions, wherein the R groups are each independently H or an organic group (which may include functionality, such as the latent reactive groups or nonreactive functional groups described below), and "M" represents a metal (preferably, ruthenium or osmium) bonded to one or more ligands in a ligand sphere). Specific examples of suitable catalysts include, but are not limited to, Grubb's ruthenium metal carbene catalyst (Compound 4, FIG. 6) and the compounds shown in FIG. 3 and disclosed in Kingsbury et al., *J. Amer. Chem. Soc.*, 121, 791–799 (1999); Schwab et al., *J. Amer. Chem. Soc.*, 118, 100–110 (1996); Dias et al., *Organometallics*, 17, 2758–2767 (1998); del Rio et al., *Tetrahedron Lett.*, 40, 1401–1404 (1999); Furstner et al., *Chem. Commun.*, 95–96 (1999); Weskamp et al., *Angew. Chem., Int. Ed. Engl.*, 37, 2490–2493 (1998); and Scholl et al., *Tetrahedron Lett.*, 40, 2247–2250 (1999). Others include those disclosed in, for example, U.S. Pat. No. 5,831,108

(Grubbs et al.), U.S. Pat. No. 5,342,909 (Grubbs et al.), U.S. Pat. No. 5,710,298 (Grubbs et al.), U.S. Pat. No. 5,312,940 (Grubbs et al.), U.S. Pat. No. 5,750,815 (Grubbs et al.), U.S. Pat. No. 5,880,231 (Grubbs et al.), U.S. Pat. No. 5,849,851 (Grubbs et al.), and U.S. Pat. No. 4,883,851 (Grubbs et al.).

A preferred group of catalysts include those that react with electron rich alkenes (as discussed in greater detail below), and preferably have at least one latent reactive group (referred to herein as a catalyst latent reactive group) and/or at least one desired nonreactive functional group. Nonreactive functional groups include, for example, natural products or analogs thereof, metal chelators, metals, fluorescent probes, solid supports, and metal surfaces.

Latent reactive groups on the catalyst are analogous to the latent reactive groups on preferred monomers in that these reactive groups do not interfere with the ROMP reaction, but allow for subsequent functionalization in a manner similar to that described in Applicants' Assignee's copending U.S. patent application Ser. No. 09/335,430, filed on even date herewith, entitled "Methods for Making Multivalent Arrays."

The catalyst latent reactive groups that are used for functionalization include electrophilic or nucleophilic groups. Examples of electrophilic latent reactive groups include, but are not limited to, acyl sulfonamides, acyl azides, epoxides, anhydrides, esters (including activated esters such as pentafluorophenyl esters and N-hydroxysuccinimidyl esters), carboxylic acids (including activated acids such as acyl halides), halides, boronic acids, ketones, aldehydes, phosphoric acid esters (mono-, di-, and ti-esters), phosphites, acyl nitrites, alkenes, and alkynes, and the like. Examples of nucleophilic latent reactive groups include, but are not limited to, amines, azides, hydroxyls, thiols, sulfones, acyl hydrazides, phosphites, hydrazines, oximes, isocyanates, thiocyanates, and the like. The stereochemistry of these groups may be defined or racemic. If desired these groups may be protected with groups such as carbamates, carbonates, thioethers, disulfides, nitro groups, and the like. Preferably, in the formula $M=CR^4R^5$, wherein M represents a metal in a ligand sphere), $R^4$ is an organic group that includes a latent reactive group, such as an azide, an epoxide, a cyano group, an acetal, a ketal, a carbamate, a thiocyanate, an activated ester, an activated acid, a hydrazine, or a hydrazone, and $R^5$ is H or an organic group, preferably, H.

Particularly preferred catalysts have the following general formula:

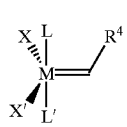

Formula II wherein M is Ru or Os, X and X' are independently an anionic ligand (preferably, halides, alkoxides, thiolates, amnides, phosphides, and acyls), and L and L' are independently neutral ligands (preferably, arenes, ketones, alkynes, carbenes, carbonyls, imides, phosphines, arsines, amines, imines, and nitriles), and $R^4$ is an organic group that includes a latent reactive group. Preferably, $R^4$ is an organic group that includes an azide, an epoxide, a cyano group, an acetal, a ketal, a carbamate, a thiocyanate, an activated ester, an activated acid, a hydrazine, or a hydrazone. Alternatively, $R^4$ is an organic group that includes a nonreactive functional group selected from natural products or analogs thereof, metal chelators, metals, fluorescent probes, solid supports, and metal surfaces.

The catalysts can be used to incorporate functionality at a terminus of the polymer to allow, for example, for coupling of two polymers together, coupling of the polymer to a solid support, or modification with small molecules, fluorescent probes, proteins, metals, metal chelators, etc. Thus, catalysts useful in the methods of the present invention can include a variety of functionality (in at least one of $R^4$ or $R^5$ in the catalyst $M=CR^4R^5$) such as: (1) catalyst latent reactive groups that can be functionalized to include terminal functional groups after polymerization; (2) nonreactive functionality that does not require further functionalization to produce the desired terminal functional groups; or (3) no functional groups. Various combinations of such catalysts can be used in the methods of the present invention.

The initial polymerization is preferably carried out in a solvent or mixture of solvents, typically one or more organic solvents, in which the monomer and catalyst are mutually soluble, although in certain embodiments, no solvent is required. Suitable solvents include substituted and unsubstituted aliphatic and aromatic hydrocarbon solvents such as chlorinated hydrocarbons, ethers, protic hydrocarbons, etc., which are unreactive under the reaction conditions. Examples include 1,2-dichloroethane, benzene, toluene, p-xylene, methylene chloride, dichlorobenzene, tetrahydrofuran, diethylether, pentane, water, methanol, etc.

The conditions of the polymerization reaction (e.g., temperature, time, atmosphere) will vary depending on the choice of monomer and catalyst, and can be selected by one of skill in the art without undue experimentation. Preferably, the ROMP reaction is carried out at a temperature of about 20° C. to about 30° C. (i.e., room temperature) or higher under an inert atmosphere (e.g., nitrogen or argon), although temperatures ranging from about −20° C. to about 125° C. are possible. Pressure is not critical, but may be varied to maintain a liquid phase reaction mixture. Reaction times can vary from several minutes to several days.

Typically, in ROMP reactions, the polymer is terminated by reacting the catalyst with a capping agent. This capping agent is typically matched to the catalyst. For ruthenium catalysts, for example, ethyl vinyl ether has been used. Although such a reagent could be used in the present invention, preferably, an electron rich alkene is used to incorporate terminal functionality in the polymer. As used herein, an electron rich alkene is one that has greater electron density than that of ethylene. In conventional capping methods, the capping agent is a vinyl ether, typically ethyl vinyl ether, that yields a material with a terminal alkene and a deactivated alpha-oxygen-substituted ruthenium metal carbene (Hillmyer, *Macromolecules*, 28, 6311–6316 (1995)).

In contrast, the capping agent of the present invention, preferably a bifunctional capping agent, incorporates an electron donating group, and preferably either a latent reactive group for subsequent functionalization (e.g., to incorporate functionality at a terminus of the polymer to allow for coupling of two polymers together, coupling to a solid support, or modification with small molecules, fluorescent probes, proteins, metals, metal chelators, etc.) or a nonreactive functional group that does not require further functionalization (i.e., it is the functionality that is desired to be incorporated into the polymer at a terminus, such as reporter groups to facilitate detection such as fluorescent groups, chemiluminescent groups, enzymes, antibodies, biotin, radioactive groups, etc.). Thus, in a similar manner to that of the catalyst, capping agents useful in the methods of the present invention can include a variety of functionality (in at least one of $R^6$ or $R^7$ in the capping agent $D-C=CR^6R^7$)

such as: (1) capping agent latent reactive groups that can be functionalized to include terminal functional groups after polymerization; (2) nonreactive functionality that does not require further functionalization to produce the desired terminal functional groups; or (3) no functional groups (as in ethyl vinyl ether). Various combinations of such capping agents can be used in the methods of the present invention.

Significantly, the catalysts and capping agents of the present invention are of general utility for controlling the strucure of the terminii of living osmium- or ruthenium-initiated ROMP reactions. Selective incorporation of single end groups into polymers will facilitate the creation of bifunctional polymers that can be appended to other oligomers, selectively immobilized, used for detection, used for quantitative binding studies, or to investigate polymer structure. The resulting materials can be conjugated to any of a number of reporter molecules, including a variety of fluorescent compounds, biotin, antibodies, enzymes, lipids, and solid supports. The functional group tolerance of the metal carbene initiator, the flexibility in catalyst selection, the generality of the post-synthetic functionalization protocol, and the versatility of the capping strategy expands significantly the scope of useful materials that can be generated by ROMP.

Typically, the capping agent has the following general structure:

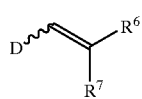

Figure 4:
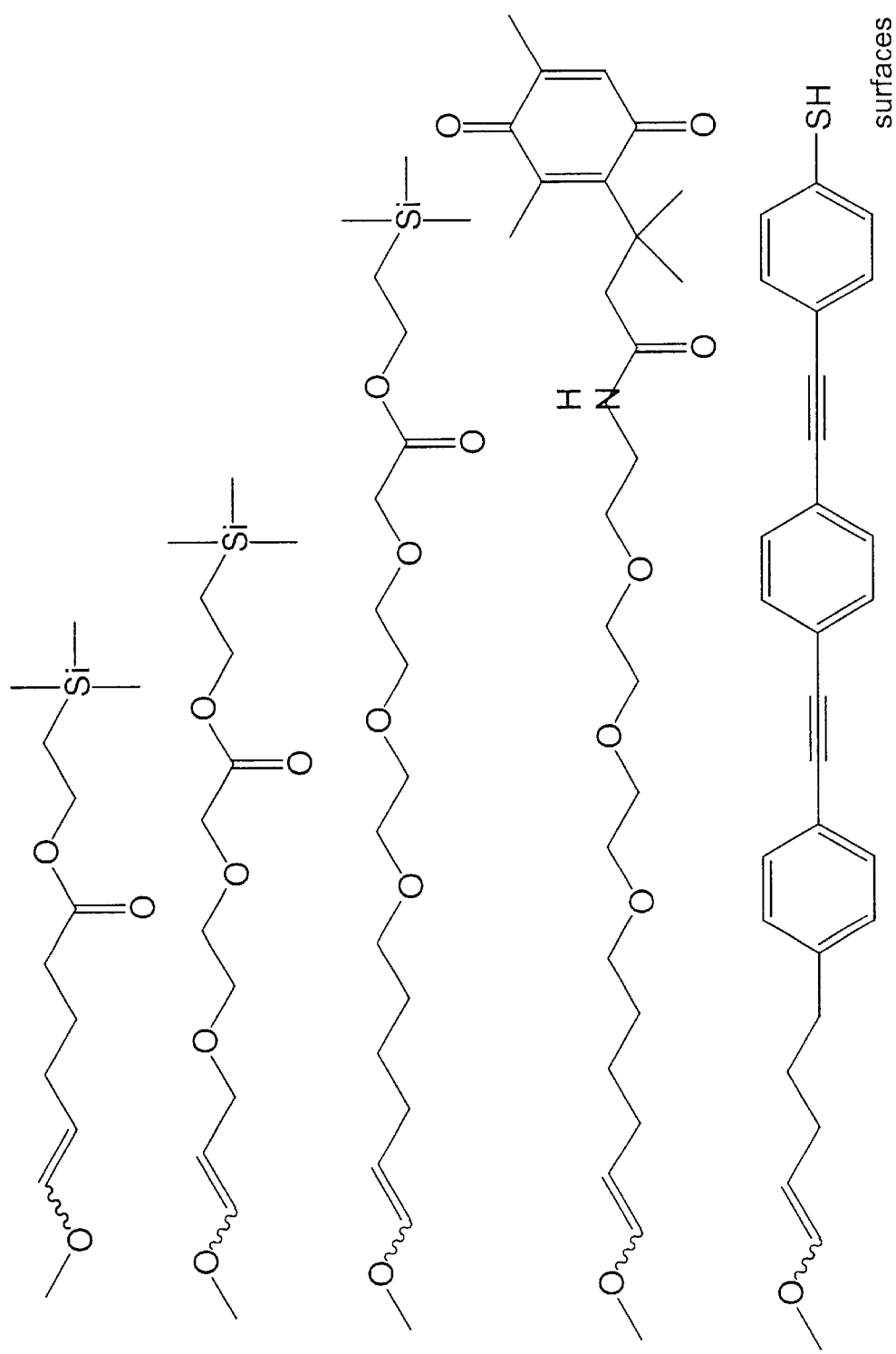
FIG. 4. Examples of capping agents containing reactive functional groups.
Figure 5:
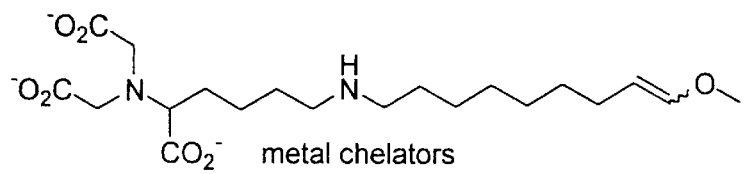
FIG. 5. Examples of capping agents containing nonreactive functional groups.
Figure 5:
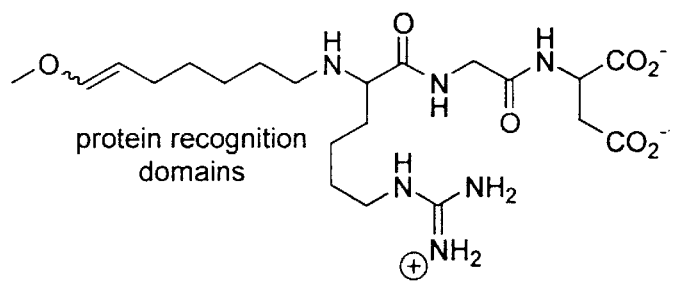
Figure 5:
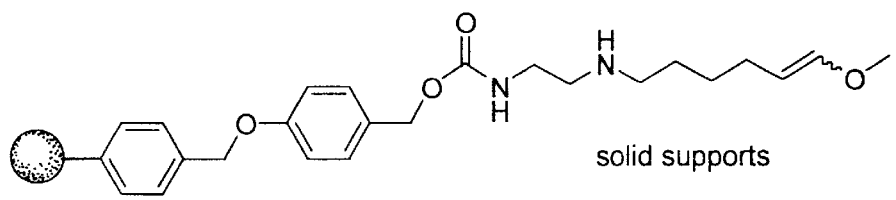

Formula III wherein D is an electron donating group (i.e., one that causes an overall increase in olefin electron density when compared to ethylene D, which can include $SR^9$, $OR^9$, halogen), $R^6$ and $R^7$ are each independently H or an organic group, at least one of which preferably includes a latent reactive group or a nonreactive functional group that does not require further functionalization. Although both $R^6$ and $R^7$ can include functionality, preferably, only one does, and more preferably, the other is H. In one preferred embodiment, $R^6$ can include a latent reactive group selected from an azide, a nitro group, a disulfide, a hydrazine, a hydrazide, a hydroxylamine, an aldehyde, a ketone, an epoxide, a cyano group, an acetal, a ketal, a carbamate, a thiocyanate, an activated ester, or an activated acid. Alternatively, in another preferred embodiment $R^6$ can be a nonreactive functional group that is selected from natural products or analogs thereof (e.g., biotin), metal chelators (such as nitrilotriacetic acid), metals (such as Zn), fluorescent probes (such as an amide derived from BODIPY FL EDA which is 4,4-difluoro-5,7-dimethyl-4-bora-3a,4a-diaza-s-indacene-3-propionyl ethylenediamine), solid supports (such as polyethylene resins), and metal surfaces (such as gold surfaces used for surface plasmon resonance (SPR)). Examples of capping agents containing reactive functional groups are illustrated in FIG. 4 and examples of capping agents containing nonreactive functional groups are illustrated in FIG. 5.

Certain preferred capping agents include both latent or nonreactive functional groups and ethylene glycol groups. Typically, these both form a part of one or $R^6$ or $R^7$. A particularly preferred example of the capping agent includes an alkyl vinyl ether linked to a protected carboxylic acid derivative via an ethylene glycol chain. Because of its design, this linker minimizes nonspecific interactions with proteins or hydrophobic molecules.

The methods of the present invention involve standard coupling techniques between capping agents and polymer chains. These coupling techniques will depend on the capping agents selected and may involve solution or solid state reaction conditions. Such techniques and conditions could be readily determined by one of skill in the art, and are similar, if not the same as, the conditions of polymerization.

Alternative to a capping agent, the polymer template can be terminally functionalized by oxidizing the catalyst, with oxygen or other oxidizing reagents, and forming an aldehyde at the terminus of the backbone of the polymer template. For example, the polymer template can simply be exposed to air or placed under an oxygen atmosphere at room temperature and pressure.

The functionalizing reagents (i.e., the compound from which the terminal functional group is derived if the catalyst and/or capping agent include a latent reactive group, or if the polymer includes a terminal aldehyde group) can include a wide variety of molecules that confer useful properties to the resultant polymer (e.g., fluorescence), as discussed above for the $R^6$ group.

The methods of the present invention involve standard coupling techniques between functionalizing reagents and polymer (or polymer templates). These coupling techniques will depend on the latent reactive groups selected and may involve solution or solid state reaction conditions depending on the solubility of the polymer template. Such techniques and conditions could be readily determined by one of skill in the art.

The resultant polymers have the following general formula:

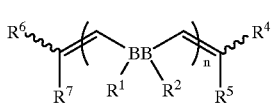

Formula IV wherein "BB" represents the backbone repeat unit, which may be cyclic or acyclic, and may be the same or different in a random or block arrangement (examples of which are disclosed in Applicants' Assignee's copending U.S. patent application Ser. No. 09/335,430, filed on even date herewith, entitled "Methods for Making Multivalent Arrays"), $R^1$ and $R^2$ are each independently H or an organic group containing the desired pendant functionality, $R^4$ and $R^5$ are each independently H or an organic group derived from the metal carbene catalyst, and $R^6$ and $R^7$ are each independently H or an organic group derived from the capping agent, and n is the average number of repeating monomer units, which can be varied by controlling the monomer to catalyst ratio. At least one of $R^4$, $R^5$, $R^6$, or $R^7$ includes a latent reactive group or a nonreactive functional group. Typically, n is at least 2 and no more than about 10,000, but there is practically no limit. As discussed above, ROMP can provide polymers of varying average lengths (i.e., varying degree of polymerization, DP) depending on the monomer to ROMP catalyst (i.e., initiator) ratios. The length of all polymers described herein are referred to as the length predicted by the monomer to initiator ratio used in the polymerization reaction.

Another preferred example of the polymer template has the following general structure:

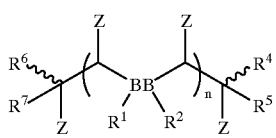

Formula V wherein BB, $R^1$, $R^2$, $R^4$, $R^5$, $R^6$, $R^7$, and n are as defined above, and each Z is independently H, OH, SH, X (a halide such as F, Br, I, Cl), or $N(R^8)_2$ (wherein each $R^8$ is independently H or an organic group). At least one of $R^4$, $R^5$, $R^6$, or $R^7$ includes a latent reactive group or a nonreactive functional group.

In the definitions of "R" groups as used herein, the term "organic group" means a hydrocarbon group (with optional elements other than carbon and hydrogen, such as oxygen, nitrogen, sulfur, phosphorus, germanium, tin, boron, and silicon, which can be in the form of various functional groups) that is classified as an aliphatic group, cyclic group, or combination of aliphatic and cyclic groups (e.g., alkaryl and aralkyl groups). In the context of the present invention, the organic groups are those that do not interfere with the formation of the polymer template or resultant polymer, unless they include the requisite reactive groups. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group (which can be aromatic or aliphatic). The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Substitution is anticipated on the organic groups of the complexes of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

For the structures illustrated herein, for each R group that can include an organic group, which can be of a significantly large size, for example, on the order of 10,000 carbon atoms, the following applies. Preferably, the organic groups of $R^1$ and $R^2$ are each independently a $C_1$–$C_{5000}$ organic group, more preferably, $C_1$–$C_{2500}$ organic group, even more preferably $C_1$–$C_{1000}$ organic group, and most preferably, $C_{1-C100}$ organic group, encompassing peptides, proteins, carbohydrates, metal chelators, natural products, etc. Preferably, the organic groups of $R^4$, $R^5$, $R^6$, and $R^7$ are each independently a $C_1$–$C_{10,000}$ organic group, more preferably, $C_1$–$C_{6000}$ organic group, even more preferably $C_1$–$C_{1000}$ organic group, and most preferably, $C_1$–$C_{500}$ organic group, encompassing antibodies, nucleic acids, peptides, proteins, carbohydrates, metal chelators, fluoresent tags, enzymes, solid supports, etc. Preferably, the organic group of $R^3$, $R^8$, and $R^9$ are each independently a $C_1$–$C_{20}$ organic group, more preferably, $C_1$–$C_{10}$ alkyl group, and most preferably $C_1$–$C_3$ alkyl moiety.

To test the modification strategy, the bifunctional capping agent 8 (FIG. 6) was designed to incorporate a masked carboxylic acid onto the end of living polymer chains. The target molecule was comprised of an enol ether linked to a protected carboxylic acid via an ethylene glycol linker. The β-trimethylsilyl (TMS) ethyl carboxylic acid protecting group serves two purposes. First, the distinct signal of the TMS group in the $^1$H NMR spectrum provides an estimate of the capping efficiency; and second, the β-TMS ethyl group can be removed under conditions that do not affect the sulfated carbohydrate recognition epitopes employed in this study. Moreover, carboxylic acids can be activated for further functionalization easily, selectively, and with high efficiency. The target capping agent 8 could be readily assembled from triethylene glycol in six steps.

Figure 6:
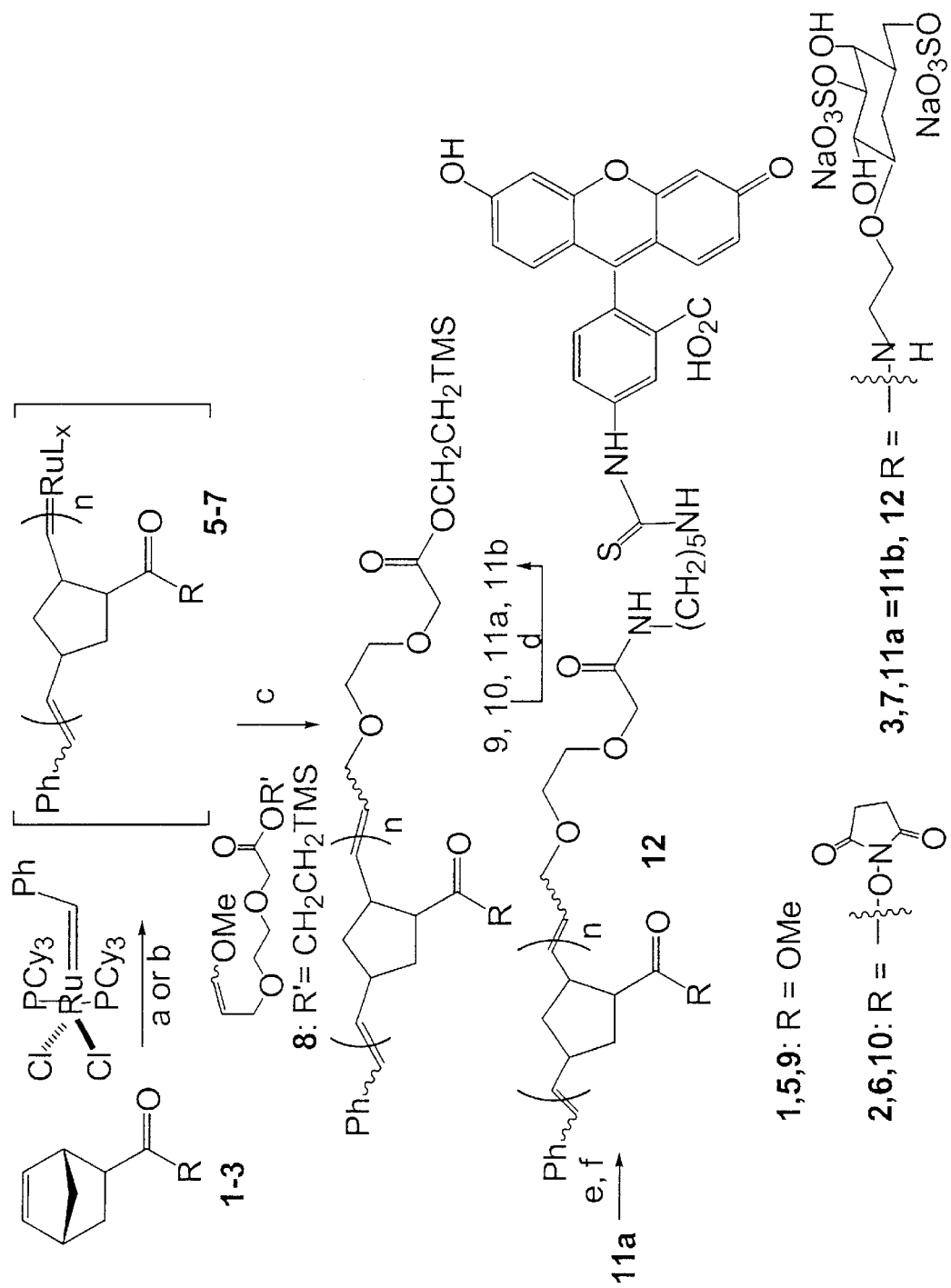
FIG. 6. Scheme for the synthesis of end-capped polymers. Reagents and conditions: for 1 and 2(a) 1,2-Dichloroethane (DCE), 30 minutes; for 3(b) Dodecyltrimethylammonium bromide (DTAB) (1.6 equivalent), 2,2-bis(hydroxymethyl)-2,2',2'-nitrilotriethanol (bis-tris) buffer (100 mM, pH 5.9), DCE, 45° C., 30 minutes; (c) excess capping agent 8 was added neat; (d) (2-aminoethyl)-3,6-O-disulfo-β-D-galactopyranoside, diisopropylcarbodiimide, Et₃N, DMF, H₂O; (e) 50 mM NaOH, 60° C., 2 hours; (f) 5-((5-aminopentyl)thioureidyl) fluorescein, EDCI, N-hydroxysulfosuccinimide, H₂O, 24 hours.

The ability of enol ether 8 to terminate ROMP reactions was evaluated in reactions of three monomers with different properties. To ascertain the reactivity of 8 under standard conditions, non-polar monomer 1 was subjected to ROMP, and an excess of compound 8 was introduced to terminate the reaction (FIG. 6). From $^1$H NMR data, comparison of the integration of the phenyl protons incorporated from the catalyst with that of the protons from the TMS group revealed that approximately 80% of the resulting polymer chains were capped to afford material 9. Initial attempts to end-label polymers bearing highly polar substituents revealed that the capping reaction was less effective for these substrates. Specifically, when the emulsion conditions required for oligomerization of polar compound 3 were used, reaction termination with enol ether 8 resulted in 11a, which was produced with a useful but more modest capping efficiency (30%) (FIG. 6). To minimize complications arising from phase transfer processes, an alternative strategy to generate polar, functionalized polymer 11b was used. Polymers containing N-hydroxysuccinimide esters, such as 10, can be assembled in organic solvents using ROMP. Subsequent post-polymerization modification by treatment of the resulting materials with a nucleophile generates a new substituted polymer. As with products from reaction of methyl ester 1, polymer 10 obtained from reaction of 3 can be terminated with capping agent 8 in efficiencies of approximately 80%. Polymer 10 could then be coupled to an amine-containing saccharide moiety to afford the 3,6-disulfogalactose derivative 11b. After purification of material 11b, the NMR spectroscopic data polymers 11a and 11b were virtually indistinguishable except for differences in the intensities of the signals arising from the capping agent. It is believed that the single phase, homogenous reaction conditions result in higher capping yields than do the emulsion polymerization conditions because the solubilities of the starting materials and products strongly influence the relative rates of various steps in polymer assembly and termination.

The importance of multivalent recognition events in biology and the utility of multivalent arrays in elucidating the features of such processes have accelerated the development of synthetic methods to generate multidentate ligands equipped with reporter groups. For example, acrylamide copolymerization can incorporate saccharide recognition elements and reporter groups, and this strategy has been used to develop materials for assaying protein-carbohydrate interactions. Alternatively, polymers possessing reporter groups have been generated by coupling a desired functional tag to a preformed polymer backbone, either using a single equivalent of the tag or by attaching a reporter group to each monomer prior to coupling to the multivalent scaffold. None of the reported synthetic routes allow for control over the length of the polymer chain or the number of reporter groups incorporated in the multivalent array.

Figure 7:
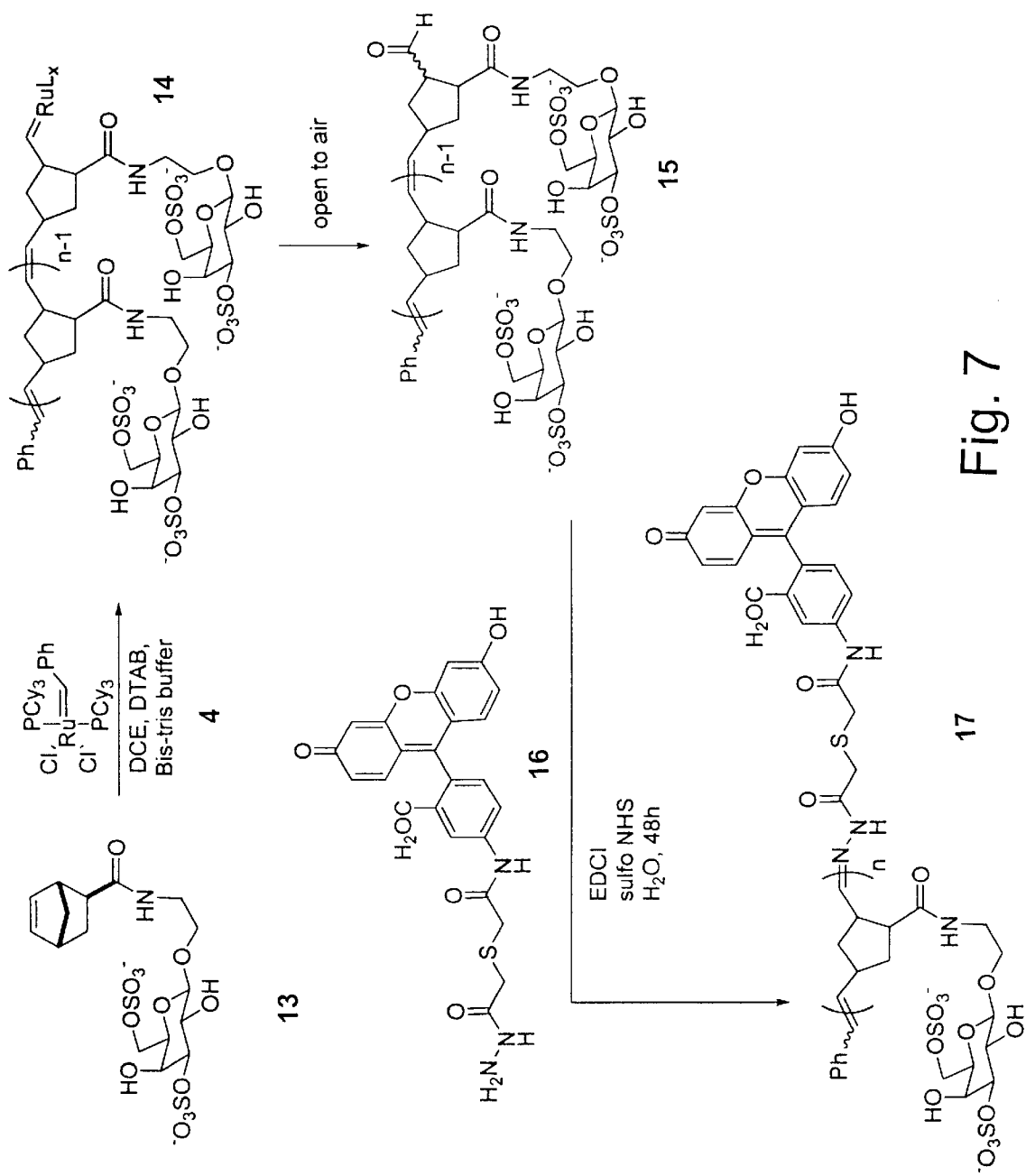
FIG. 7. Scheme for the synthesis of a fluorescent neoglycopolymer via a terminal aldehyde.

In addition to adding an electron rich alkene, the polymer chain can be capped with a functional group via oxidation of the terminal metal carbene. For example, exposure of polymers in which the active metal carbene center is present at the end of the growing chain to oxygen results in a terminal aldehyde on the polymer chain. This strategy was explored in parallel to the method just described with enol ether 8. The sulfated galactose monomer 13 was subjected to the ROMP catalyst 4 and following consumption of the monomer, the reaction was opened to air to yield polymer 15 (FIG. 7). This approach relies on efficient capping with oxygen and subsequent hydrazone, hydrazide, or hydroxyl amine formation. This method uses fewer steps to obtain the final product; however, the capping efficiency is more difficult to monitor than in the case of polymers 9, 10, and 11a and 11b.

To demonstrate the utility of the synthetic scheme of the present invention for selective incorporation of a single reporter, end-labeled neoglycopolymers were coupled to a fluorescent reporter group through the end-label. These fluorescent neoglycopolymers were designed to allow studies of the interactions of the polymers with cell surface L-selectin.

L-selectin, a member of the selectin family of cell adhesion molecules, facilitates the recruitment of white blood cells to sites of tissue damage. Certain sulfated, saccharide-containing neoglycopolymers related to 11a are potent inhibitors of selectin function. It is believed that these neoglycopolymers inhibit protein function by binding to L-selectin on the cell surface. By transforming 11a and 15 into reporter ligands 12 and 17 respectively, neoglycopolymer binding to cell surface L-selectin could be directly investigated.

The initial step in the generation of 12 involved unmasking the carboxylic acid by saponification of the β-trimethylsilyl ethyl ester (FIG. 6). A fluorescein derivative (5-((5-aminopentyl)thioureidyl) fluorescein or fluorescein cadaverine) was attached through amide bond formation. The resulting conjugate was isolated by size exclusion and cation exchange chromatography to afford fluorescein-modified oligomer 12. Polymer 15 could be directly subjected to 5-(((2-(carbohydrazino)methyl)thio)acetyl) aminofluorescein), a hydrazine fluorescein derivative, 16, to yield the desired fluorescent tagged polymer 17 (FIG. 7).

The ability of polymers 12 and 17 to bind Jurkat cells (a human acute T cell leukemia line) displaying L-selectin was examined using fluorescence microscopy (FIG. 8). For comparison, cells were labeled with a fluorescein-conjugated antibody to L-selectin. Both the antibody and the polymer bound cells at localized sites, producing similar, punctate fluorescence patterns. The observed patterns are consistent with observations that L-selectin is not randomly distributed on the leukocyte surface but is localized to specific regions of the cell termed microvilli. The binding was dependent on the presence of cell surface L-selectin, as neither the fluorescent polymer nor anti-L-selectin antibody was observed to bind to L-selectin deficient cells (an HL60 cell line, data not shown). Similar results were seen using the aldehyde capped polymer 17 (FIG. 8).

These results suggest that neoglycopolymers bind specifically to L-selectin on the cell surface. One would expect general cell surface staining if ligand 12 was binding non-specifically. Moreover, further microscopy studies suggest that the significant biological activities of these glycoprotein mimics are mediated through multivalent contacts. This data highlights the utility of probes 12 and 17 for visualizing cell surface recognition events.

Objects and advantages of this invention are further illustrated by the following examples, but the particular materials and amounts thereof recited in these examples, as well as other conditions and details, should not be construed to unduly limit this invention.

EXAMPLES

Materials: Bis(tricyclohexylphosphine)benzylidene ruthenium(IV)dichloride was obtained from Strem Chemicals, Inc. (Newburyport, Mass.). 5-((5-aminopentyl) thioureidyl) fluorescein (fluorescein cadaverine) was purchased from Molecular Probes (Eugene, Oreg.). Cell culture media RPMI 1640 and fetal calf serum were from Gibco BRL (Gaithersburg, Md.). Penicillin, streptomycin, L-glutamine, and sodium pyruvate were from Sigma (St. Louis, Mo.). Fluorescein-labeled anti L-selectin antibody (DREG-56) was purchased from Pharmingen (San Diego, Calif.). VectaShield was from Vector Laboratories (Burlingame, Calif.). All other reagents were purchased from Aldrich Chemical Co., Milwaukee, Wis., unless otherwise specified. All solvents were purchased either from Aldrich Chemical Co., or Fisher Scientific, Pittsburgh, Pa.

General Methods: All nonaqueous reactions were carried out in oven-dried glassware under a nitrogen atmosphere. Reaction solvents were distilled from sodium/benzophenone (tetrahydrofuran), calcium hydride (dichloromethane, triethylamine, dichloroethane), or under reduced pressure over type 4 Å molecular sieves (DMSO). Reactions were monitored by thin-layer chromatography (TLC) on 0.25 mm precoated Merck Silica Gel 60 $F_{254}$ (VWR Scientific, So. Plainfield, N.J.), visualizing with ultraviolet light, p-anisaldehyde stain (15 ml p-anisaldehyde, 10 ml acetic acid, 10 ml sulfuric acid, 350 ml ethanol), or potassium permanganate stain (3 grams $KMnO_4$, 20 grams $K_2CO_3$, 5 ml of 5% aqueous NaOH, 200 ml water). Flash column chromatography was performed on Merck Silica Gel 60 (230–400 mesh, Scientific Adsorbents Inc., Atlanta, Ga.) using distilled reagent grade hexanes and dichloromethane and ACS grade ethyl acetate, methanol, and chloroform. When handling acid-sensitive compounds, chloroform and dichloromethane were neutralized by filtration through basic alumina immediately prior to use. Infrared spectra were recorded on a Mattson FTIR spectrometer. Mass spectral data were obtained by Liquid Secondary Ion Mass Spectrometry (LSIMS) on a Micromass Autospec Mass Spectrometer (3-nitrobenzoic acid with added sodium iodide (3-NBA+NaI) matrix). $^1$H and $^{13}$C NMR spectra were recorded on a Bruker AC-300 spectrometer and are referenced to residual solvent peaks (CDCl$_3$: $^1$H: δ 7.24, $^{13}$C: δ 77.0; D$_2$O: $^1$H: δ 4.67) or to an internal reference of tetramethylsilane in CDCl$_3$ ($^1$H: δ 0.00). $^1$H—$^1$H couplings are assumed to be first order, and peak multiplicity is reported as s (singlet), d (doublet), t (triplet), q (quartet), m (multiplet), or b (broad).

Synthesis of Bifunctional Capping Agent 8

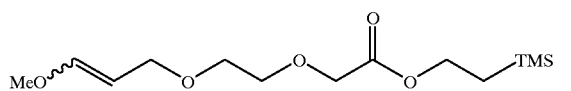

8

2-(2-(2-benzyloxy)ethoxy)ethoxy)ethanol

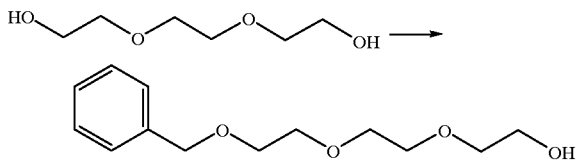

Benzyl bromide (7.9 mL, 66.6 mmol) was added to a solution of triethylene glycol (8.9 mL, 66.6 mmol) in 50% aqueous NaOH (5.3 mL), and the mixture was stirred at room temperature for 24 hours. The reaction was diluted with H$_2$O (75 mL) and extracted with Et$_2$O (4×100 mL). The combined organic extracts were dried over Na$_2$SO$_4$, concentrated, and purified by flash column chromatography (silica, EtOAc), affording 2-(2-(2-benzyloxy)ethoxy)ethoxy)ethanol (6.14 g, 38%). R$_f$=0.6 (EtOAc); IR (neat): 3500–3400, 2900–2700, 1751, 1633, 1613, 1453, 1349, 1246, 1100, 1069 cm$^{-1}$; $^1$HNMR (300 MHz, CDCl$_3$): δ 7.35–7.26 (m, 5H), 4.57 (s, 2H), 3.73–3.59 (m, 12H), 2.50 (b, 1H); $^{13}$C NMR (75 MHz, CDCl$_3$): δ 138.1, 128.4, 127.8, 127.7, 73.3, 72.6, 70.7, 70.6, 70.4, 69.4, 61.7. 10-Phenyl-3,6,9-trioxadecanoic acid

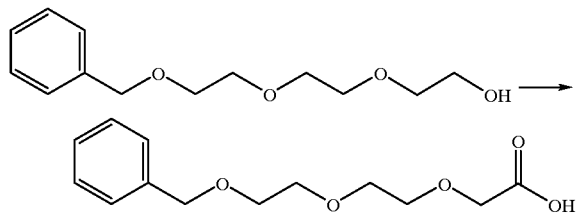

Chromium trioxide (3.33 g, 33.30 mmol) was added to 1.5 M H$_2$SO$_4$ (4.4 mL) at 0° C. A solution of 2-(2-(2-benzyloxy) ethoxy)ethoxy)ethanol (2.00 grams, 8.32 mmol) in acetone (110 mL) was added, and the reaction was stirred for 5 hours at room temperature. The solution was extracted with Et$_2$O (5×100 mL) and the combined extracts were washed with saturated NaCl (3×50 mL) and concentrated to a volume of 20 mL. Extraction with 5% NaHCO$_3$ (2×20 mL) was followed by acidification of the aqueous extracts to pH=2 with concentrated HCl and back extraction of the aqueous solution with Et$_2$O (3×50 mL). The combined organic extracts were washed with saturated NaCl (3×20 mL). Concentration provided 10-phenyl-3,6,9-trioxadecanoic acid (1.71 g, 81%). R$_f$=0.1–0.4 (10% MeOH/CH$_2$Cl$_2$); IR (neat): 3500, 3453, 2900–2700, 1751, 1739, 1629, 1614, 1453, 1353, 1245, 1204, 1120, 1100, 1026 cm$^{-1}$; $^1$H NMR (300 MHz, CDCl$_3$): δ 10.06,(b, 1H), 7.35–7.25 (m, 5H), 4.57 (s, 2H), 4.17 (s, 2H), 3.77–3.60 (m, 8H); $^{13}$C NMR (75 MHz, CDCl$_3$): δ 138.1, 128.4, 127.8, 127.7, 73.3, 72.6, 70.7, 70.6, 70.4, 69.4, 61.7.

10-Phenyl-3,6,9-trioxadecanoic acid 2-(trimethylsilyl)ethyl ester

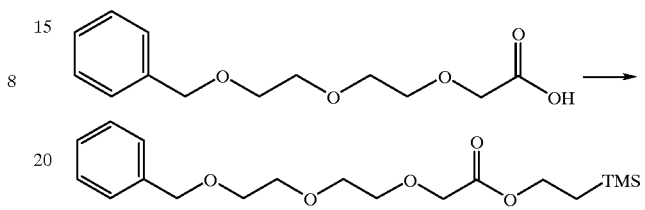

10-Phenyl-3,6,9-trioxadecanoic acid (1.71 g, 6.71 mmol) was dissolved in CH$_2$Cl$_2$ (13.4 mL) and the solution was cooled to 0° C. 1-(3-dimethylaminopropyl)-3-ethylcarbodiimide hydrochloride (EDCI) (1.41 g, 7.38 mmol) and N,N-dimethylaminopyridine (DMAP) (41.0 mg, 0.34 mmol) were added, and the suspension was stirred for 10 minutes at 0° C. 2-(Trimethylsilyl)ethanol (872.4 mg, 7.38 mmol) was added dropwise via syringe, and the solution was stirred for 20 minutes while warming to room temperature. The reaction was quenched with H$_2$O and extracted with Et$_2$O (3×50 mL). The combined Et$_2$O extracts were washed sequentially with 10% HCl (1×50 mL), 5% NaHCO$_3$ (1×50 mL), and saturated NaCl (1×50 mnL), and dried over Na$_2$SO$_4$. Concentration followed by flash chromatography (silica, 4:1 hexanes/EtOAc) afforded 10-phenyl-3,6,9-trioxadecanoic acid 2-(trimethylsilyl)ethyl ester (2.32 g, 97% yield). R$_f$=0.26 (4:1 hexanes/EtOAc); IR (neat): 3500–3400, 3000–2700, 1751, 1733, 1615, 1455, 1250, 1148, 1124 cm$^{-1}$; $^1$H NMR (300 MHz, CDCl$_3$): δ 7.32–7.23 (m, 5H), 4.54 (s, 2H), 4.24–4.18 (m, 2H), 4.10 (s, 2H), 3.72–3.59 (m, 8H), 1.01–0.95 (m, 2H), 0.01 (s, 9H); $^{13}$C NMR (75 MHz, CDCl$_3$): δ 170.5, 138.2, 128.3, 127.6, 127.5, 73.2, 70.8, 70.6, 69.4, 68.8, 63.0, 17.3, −1.6; LRMS (LSIMS, 3-NBA): m/z 377.2 [M+Na$^+$, calc'd for C$_{18}$H$_{30}$O$_5$NaSi 377.5].

3,6-Dioxa-8-hydroxy-octanoic acid 2-(trimethylsilyl)ethyl ester

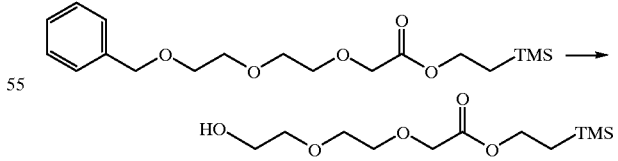

20% Pd(OH)$_2$/C (100 mg, Aldrich) was added to a solution of 10-phenyl-3,6,9-trioxadecanoic acid 2-trimethylsilyl (ethyl) ester (500 mg, 1.4 mmol) in absolute EtOH (14 mL, AAPER Alcohol and Chemical Co., Shelbyville, Ky.). The solution was shaken under 50 psi H$_2$ for 6 hours, filtered through a pad of CELITE (EtOH eluent), and concentrated under reduced pressure to afford 3,6-dioxa-8-hydroxy-octanoic acid 2-trimethylsilyl(ethyl) ester (284.4 mg, 77%).

$R_f$=0.29 (2:1 EtOAc/hexanes); IR (neat): 3500–3400, 2952, 2894, 2872, 1750, 1629, 1615, 1456, 1428, 1250, 1200, 1148, 1124, 1064 cm$^{-1}$; $^1$H NMR (300 MHz, CDCl$_3$): δ 4.26–4.19 (m, 2H), 4.11 (s, 2H), 3.75–3.59 (m, 8H), 2.65 (b, 1H), 1.02–0.95 (m, 2H), 0.02 (s, 9H); $^{13}$C NMR (75 MHz, CDCl$_3$): δ 170.6, 72.4, 70.8, 70.2, 68.6, 63.2, 61.5, 17.3, -1.6; LRMS (LSIMS, 3-NBA): m/z 287.1 [M+Na$^+$, calc'd for C$_{11}$H$_{24}$O$_5$NaSi 287.4].

3,6-Dioxa-8-al-octanoic acid 2-(trimethylsilyl)ethyl ester

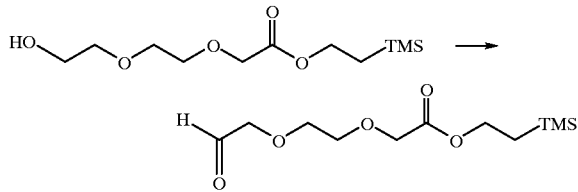

3,6-Dioxa-8-hydroxy-octanoic acid 2-trimethylsilyl (ethyl) ester (250 mg, 0.95 mmol) was dissolved in CH$_2$Cl$_2$ (4.7 mL) and the solution was cooled to 0° C. Dimethyl sulfoxide (135 μL, 1.9 mmol) was added via syringe, followed by the rapid addition of solid P$_2$O$_5$. After 30 minutes at 0° C., Et$_3$N (460 μL, 3.3 mmol) was added and the reaction was stirred for 30 min at 0° C. The reaction was quenched with 10% HCl (10 mL) and extracted with CH$_2$Cl$_2$ (3×20 mL). The combined organic extracts were washed with H$_2$O (1×25 mL) and saturated NaCl (1×25 mL), and dried over Na$_2$SO$_4$. Purification by flash chromatography (silica, 1:1 hexanes/EtOAc) afforded the product (216.0 mg, 82%). $R_f$=0.29 (1:1 hexanes/EtOAc); IR (neat): 3500–3400, 2957, 2922, 2854, 1749, 1734, 1646, 1456, 1260, 1098 cm$^{-1}$; $^1$H NMR (300 MHz, CDCl$_3$): δ 9.71 (s, 1H), 4.25–4.19 (m, 2H), 4.16 (d, J=0.7 Hz, 2H), 4.10 (s, 2H), 3.75 (s, 4H), 1.01–0.96 (m, 2H), 0.02 (s, 9H); $^{13}$C NMR (75 MHz, CDCl$_3$): δ 200.6, 170.4, 76.8, 71.2, 71.0, 68.8, 63.2, 17.4, -1.5; LRMS (LSIMS, 3-NBA): m/z 285.1 [M+Na$^+$, calc'd for C$_{11}$H$_{22}$O$_5$NaSi 285.4].

3,6,10-Trioxa-8,9-ene-undecanoic acid 2-(trimethylsilyl) ethyl ester

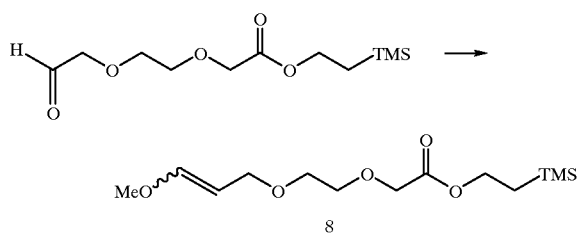

Potassium tert-butoxide (36.3 mg, 0.30 mmol) was added to a suspension of (methoxymethyl)triphenylphosphonium chloride (117.6 mg, 0.34 mmol) in THF (2.0 mL) at 0° C. The dark red solution was stirred at 0° C. for 5 minutes. 3,6-dioxa-8-al-octanoic acid 2-trimethylsilyl(ethyl) ester (42.5 mg, 0.16 mmol) was added dropwise as a 1M solution in THF (160 μL), during which the solution turned from dark red to pale yellow. The reaction was quenched with saturated NaCl (5 mL) and extracted with Et$_2$O (3×15 mL). The combined Et$_2$O extracts were washed with H$_2$O (1×20 mL) and dried over Na$_2$SO$_4$. Concentration followed by flash chromatography (silica, 9:2 hexanes/EtOAc) afforded 3,6,10-trioxa-8,9-ene-undecanoic acid 2-trimethylsilyl(ethyl) ester 8 (27.9 mg, 59%). $R_f$=0.21 (5:1 hexanes/EtOAc); IR (neat): 2952, 2932, 2898, 2860, 1752, 1732, 1660, 1457, 1251, 1214, 1197, 1176, 1147, 1102, 859, 838 cm$^{-1}$; $^1$H NMR (500 MHz, CDCl$_3$): δ 6.52 (d, J=13.1 Hz, 1H), 6.00 (dt, J=6.5, 1.1 Hz, 1H), 4.87 (dt, J=12.5, 7.5 Hz, 1H), 4.53 (td, J=7.0, 6.5 Hz, 1H), 4.24–4.17 (m, 4H), 4.10 (s, 2H), 4.09 (s, 2H), 4.07 (dd, J=7.3, 1.2 Hz, 2H), 3.92 (dd, J=7.4, 0.9 Hz, 2H), 3.71–3.54 (m, 8H), 3.58 (s, 3H), 3.53 (s, 3H), 1.01–0.94 (m, 4H), 0.01 (s, 18H); $^{13}$C NMR (75 MHz, CDCl$_3$): δ 170.6, 170.5, 151.5, 149.1, 102.7, 98.7, 70.9, 70.9, 69.0, 68.8, 68.7, 68.5, 63.8, 63.0, 59.8, 55.9, 17.4, -1.6; LRMS (LSIMS, 3-NBA): m/z 313.2 [M+Na$^+$, calc'd for C$_{13}$H$_{26}$O$_5$NaSi 313.4].

Synthesis of Polymer 9

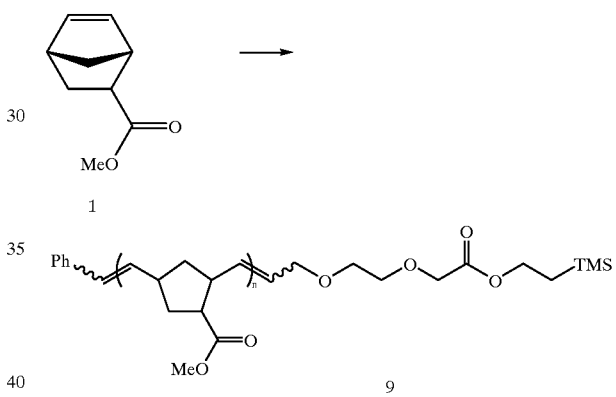

1,2-Dichloroethane (DCE) was deoxygenated by four freeze-pump-thaw (FPT) cycles. A solution of ruthenium catalyst 4 in DCE (100 μL) was added to a solution of norbornene monomer 1 (15 mg, 0.10 mmol) in DCE (400 μL). The red mixture was stirred for 30 minutes at room temperature. Capping agent 8 (30 μL) was added neat, and the reaction was stirred at room temperature for 18 hours. The mixture was concentrated, dissolved in a small amount of CH$_2$Cl$_2$ and filtered through a short pad of silica gel to remove excess capping agent 8. The remaining material was eluted from the silica gel with EtOAc, and the solution was concentrated and dried. The clear, solid material was washed with hexanes (3×) and dried to afford polymer 9 (9.6 mg, 64%).

Synthesis of Polymer 11b

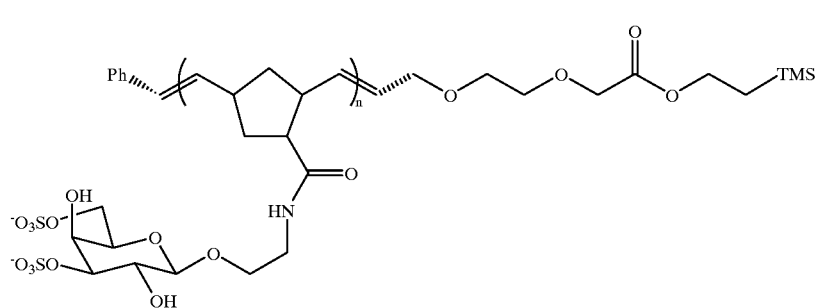

Synthesis of Polymer 10

DCE was deoxygenated by four freeze-pump-thaw cycles. A solution of ruthenium catalyst 4 (3.3 mg, 0.004 mmol) in DCE (40 μL) was added to a solution of norbornene monomer 2 (15 mg, 0.064 mmol) in DCE (280 pL). The mixture was stirred for 30 minutes at room temperature. Capping agent 8 (13.5 μL) was added neat, and the reaction was stirred at room temperature for 18 hours. The mixture was concentrated, dissolved in a small amount of $CH_2Cl_2$, and filtered through a short pad of silica gel to remove catalyst-derived impurities and excess capping agent. The solution was concentrated under reduced -continued

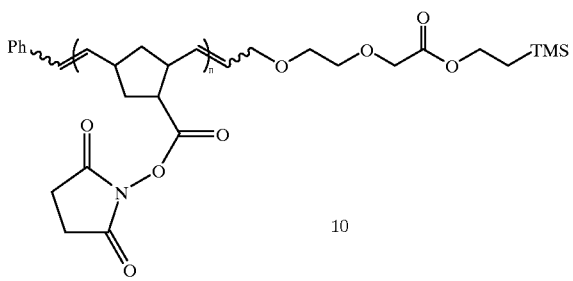

pressure and was used without purification in the coupling to 3,6-disulfo galactose amine.

Synthesis of Polymer 11b

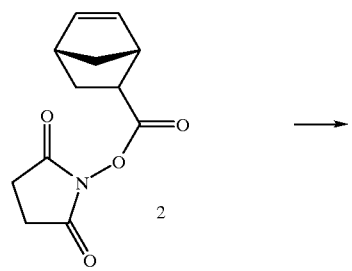

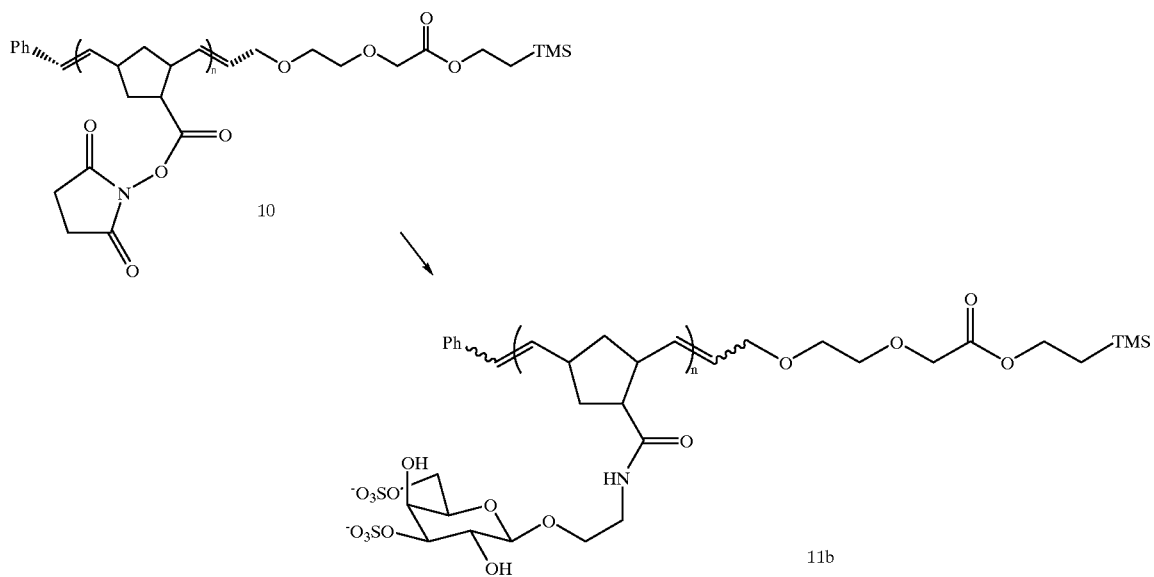

Diisopropylcarbodiimide (DIC) (5 μL, 0.032 mmol) was added to a solution of polymer 10 (7.5 mg) DMF (320 μL). (2-aminoethyl)-3,6-O-disulfo-β-D-galactopyranoside (16.7 mg, 0.048 mmol) was added as a 1 M solution in $H_2O$ (48 μL), and $Et_3N$ (8.9 μL, 0.064 mmol) was added. The reaction was stirred at room temperature for approximately 40 hours and then diluted with $H_2O$ (approximately 1 mL). The aqueous solution was extracted with $CHCl_3$ (3×2 mL) and concentrated under reduced pressure. The residue was washed with MeOH (3×2 mL), affording neoglycopolymer 11b.

Synthesis of Fluorescein-Labeled Neoglycopolymer 12 mer 3 (15 mg, 0.027 mmol), dodecyltrimethyl ammonium bromide (DTAB) (13.5 mg, 0.044 mmol) and 2,2-bis (hydroxymethyl)-2,2',2"-nitrilotriethanol (bis-tris) buffer (91 μL, 100 mM, pH 5.9) were deoxygenated by subjecting each solution to four freeze-pump-thaw (FPT) cycles. The deoxygenated dichloroethane (45 μL) was added to a vial containing ruthenium metal carbene 4 (1.5 mg, 0.0018 mmol) under nitrogen, and the purple solution was added to the reaction vessel containing the buffered solution of monomer and DTAB. The reaction was heated to 40–45° C. for 20 minutes, capping agent 8 (10 μL) was added neat, and the mixture was stirred at 40–45° C. for 15 minutes. The reaction was allowed to cool to room temperature and stirred for 6

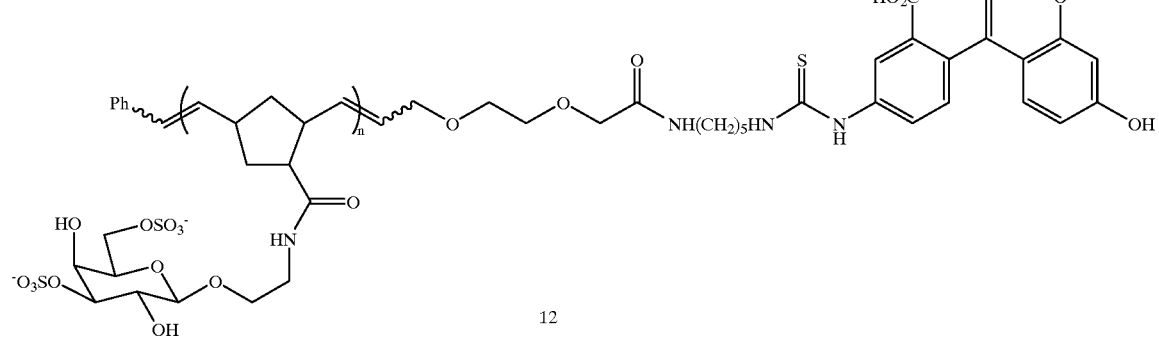

12

Synthesis of Polymer 11a

Dichloroethane (DCE) and, in a separate reaction vessel, a solution of the sodium salt of 3,6-disulfo galactose mono-

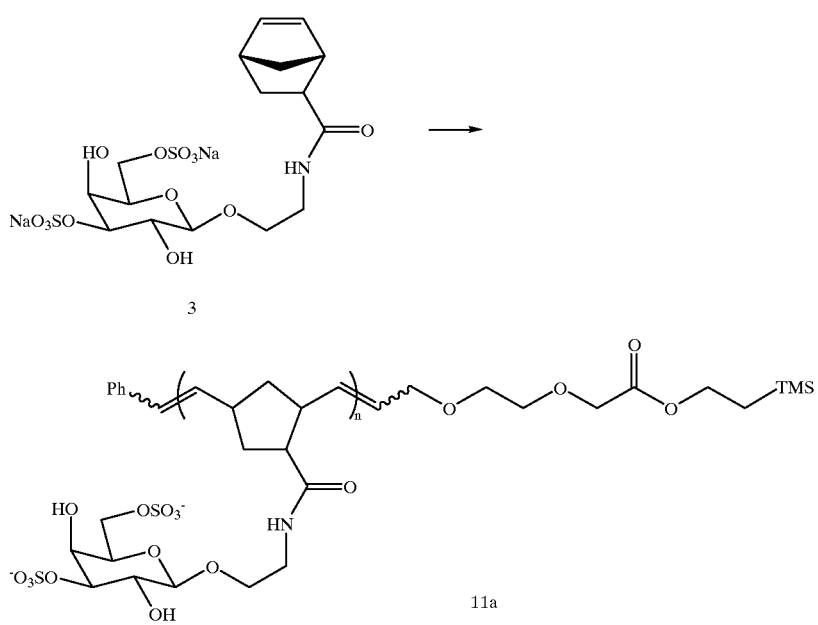

hours. The crude mixture was diluted with H₂O and MeOH until the solution was one phase and the final volume was approcimately 1 mL. The polymer was purified by cation exchange chromatography (SEPHADEX-SP C-25, Pharmacia, Piscataway, N.J.; 0.75×4.0 cm; Na⁺, H₂O eluent), concentration to dryness, suspension of the residue in MeOH and centrifugation (3×). The MeOH insoluble material was dissolved in H₂O and concentration to dryness afforded capped, polymer 11a as a light brown, flaky solid in moderate yields (60–80%).

Deprotection of Polymer 11a

Capped polymer 11a was dissolved in H₂O (95 μL), and 1 M NaOH (5 μL) was added. The flask was fitted with a cold finger, and the solution was heated at 60° C. for 2 hours. After cooling to rt, the solution was diluted with H₂O to a final volume of 1 mL and neutralized (AMBBRLYST 15 strongly acidic, macroreticular resin, Aldrich). The mixture was filtered through a small plug of glass wool to remove the resin and then concentrated to dryness, affording the deproteeted polymer.

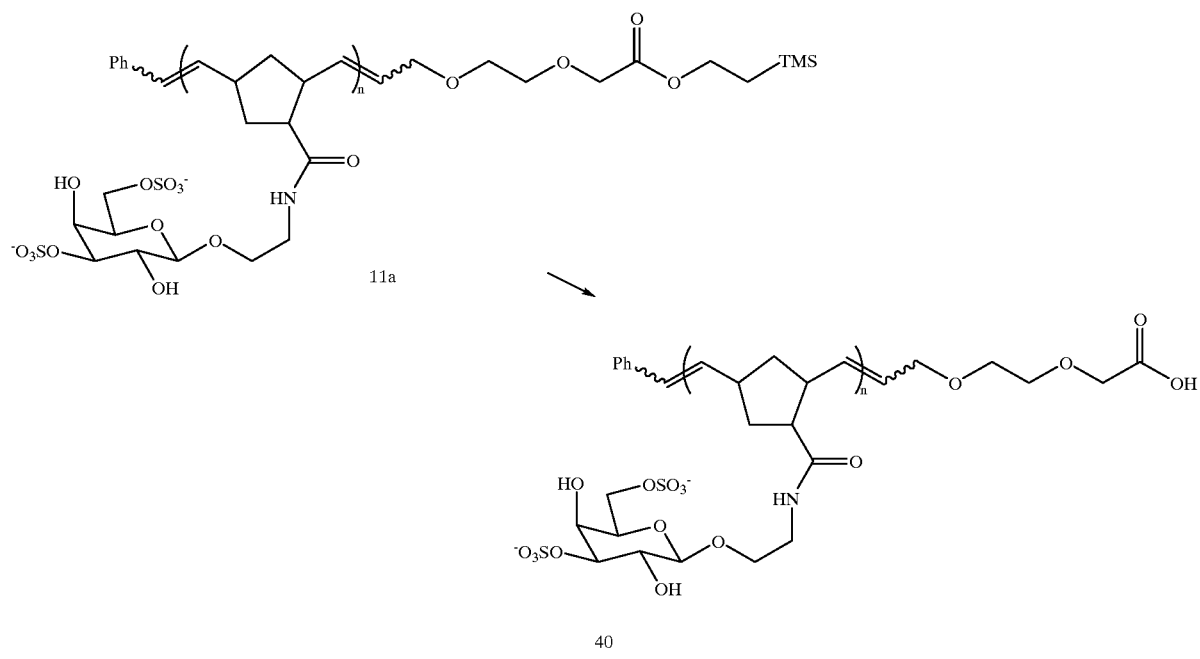

Synthesis of Conjugate 12

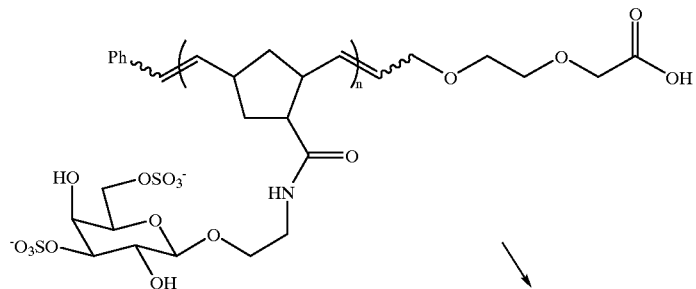

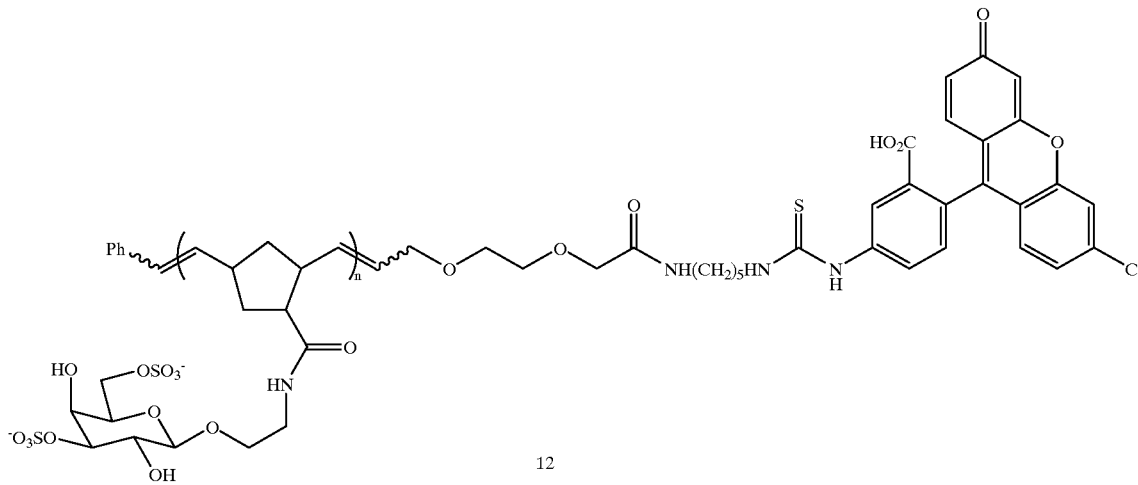

12

Deprotected polymer (3.2 mg) was dissolved in H$_2$O (60 μL). EDCI (0.8 mg, 0.004 mmol) and N-hydroxysulfosuccinimide (sulfo NHS, Pierce, Roickford, Ill.) (0.9 mg, 0.004 mmol) were added, and the mixture was incubated at room temperature for 5 minutes. 5-((5-aminopentyl)thioureidyl) fluorescein (fluorescein cadaverine) (1.3 mg, 0.002 mmol) was added and the reaction was stirred at room temperature in the dark for 24 hours. The fluorescein-coupled polymer was purified by cation exchange chromatography (SEPHADEX-SP C-25, Pharmacia; 0.75×4.0 cm; Na$^+$, H$_2$O eluent) and size exclusion chromatography (SEPHADEX G-25, Pharmacia, 0.75× 22.0 cm, H$_2$O eluent), affording fluorescein-coupled polymer 12 (2.2 mg, 69%).

Synthesis and Modification of Oxygen-terminated polymer 17

DCE and, in a separate reaction vessel, a solution of the sodium salt of 3,6-disulfo galactose monomer 13 (15 mg, 0.027 mmol) and DTAB (13.5 mg, 0.044 mmol) in bis-tris buffer (91 μL, 100 mM, pH 5.9) were deoxygenated by subjecting each solution to four freeze-pump-thaw cycles. The deoxygenated DCE (45 μL) was added to a vial containing the ruthenium carbene 4 (1.5 mg, 0.0018 mmol) under nitrogen, and the purple solution was added to the reaction vessel containing the buffered solution of monomer and DTAB. The reaction was heated to 60° C. for 2.5 hours, allowed to cool to room temperature, and then opened to the atmosphere and stirred for 12 hours. 5-(((2-(carbohydrazino) methyl)thio)acetyl)aminofluorescein 16 (Molecular Probes, Eugene, OR, 2.5 mg, 0.0051 mmol) was added and the reaction was stirred at room temperature in the dark for 48 hours. The fluorescein-coupled polymer was purified by cation exchange chromatography (SEPHADEX-SP C-25, Pharmiacia; 0.75×4.0 cm; Na$^+$, H$_2$O eluent) and washing with MeOH (3×), affording fluorescein-coupled polymer 17 (8.6 mg, 57%).

Fluorescence Microscopy

Jurkat cells were cultured at 37° C. and 5% CO$_2$ in RPMI 1640 with 10% fetal calf serum, 100 U/mL penicillin, 100 μg/mL streptomycin, 2 mM L-glutamine, and 1 mM sodium pyruvate. Cell viability was greater than 95% as determined by staining with 0.4% Trypan Blue. For each experiment, 5×10$^5$ live cells were used. Jurkat cells were centrifuged at 750×g for 1 minutes, supernatant culture media was decanted and the cells were resuspended in 1 mL cold PBS. The cells were centrifuged again and resuspended in 100 μL of cold PBS. FITC-labeled anti-L-selectin antibody or fluorescein labeled polymer 12 or fluorescein polymer 17 were added. The final concentration of the polymer was 4 mM in galactose residues. Cells were incubated at 4° C. for 30 minutes and washed twice with 2 mL cold PBS. Cells were fixed in 1 mL of fresh 2% HEPES buffered paraformaldehyde at 4° C. for 30 minutes and washed twice with 2 mL cold PBS. Cells were centrifuged and resuspended in 50 mL of cold PBS. The cell solution was then applied to cover slips and mounted on clean glass slides with 5 mL of VectaShield anti-quenching agent. Slides were incubated overnight at 4° C. and then viewed under an oil-immersion lens (630×) on a Zeiss Axioskop microscope (Zeiss, Germany) outfitted with a FITC-selective filter and Princeton Instruments MicroMax camera. Images were acquired using IPLab Spectrum software (Signal Analytics Corporation (Vienna, Va.)). Images presented are representative of the results obtained from a minimum of 4 independent trials.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of preparing a telechelic polymer, the method comprising the steps of:

polymerizing at least one monomer comprising at least one group that can be polymerized through ring-opening metathesis polymerization in the presence of at least one ruthenium or osmium carbene catalyst to form a polymer template; and combining the polymer template with at least one functionalized capping agent containing an electron donating group under conditions effective to react the polymer template with the capping agent to form a terminally functionalized polymer.

2. The method of claim 1 wherein the functionalized capping agent comprises a latent reactive group for subsequent reaction with a functionalizing reagent.

3. The method of claim 2 wherein the functionalized capping agent has the following formula:

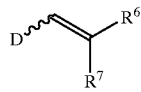

Formula III wherein D is an electron donating group and $R^6$ is an organic group that includes a latent reactive group selected from the group consisting of an azide, a nitro group, a disulfide, a hydrazine, a hydrazide, a hydroxylamine, an aldehyde, a ketone, an epoxide, a cyano group, an acetal, a ketal, a carbamate, a thiocyanate, an activated ester, an activated acid, and combinations thereof, and $R^7$ is H or an organic group.

4. The method of claim 1 wherein the functionalized capping agent comprises a nonreactive functional group.

5. The method of claim 4 wherein the functionalized capping agent has the following formula:

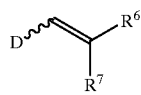

Formula III wherein D is an electron donating group and $R^6$ is an organic group that includes a nonreactive functional group selected from the group consisting of natural products or analogs thereof, metal chelators, metals, fluorescent probes, solid supports, metal surfaces, and combinations thereof, and $R^7$ is H or an organic group.

6. The method of claim 1 wherein the polymer is a monotelechelic polymer.

7. A method of preparing a telechelic polymer, the method comprising the steps of:
polymerizing at least one monomer comprising at least one group that can be polymerized through ring-opening metathesis polymerization in the presence of at least one functionalized ruthenium or osmium carbene catalyst to form a functionalized polymer template; and
combining the functionalized polymer template with at least one capping agent containing an electron donating group under conditions effective to react the functionalized polymer template with the capping agent to form a terminally functionalized polymer.

8. The method of claim 7 wherein the functionalized carbene catalyst comprises a latent reactive group for subsequent reaction with a functionalizing reagent.

9. The method of claim 8 wherein the functionalized carbene is represented by $M=CR^4R^5$, wherein $R^4$ is an organic group that includes a latent reactive group, $R^5$ is H or an organic group, and M represents ruthenium or osmium in a ligand sphere.

10. The method of claim 9 wherein $R^4$ is an organic group that includes a latent reactive group selected from the group consisting of an azide, an epoxide, a cyano group, an acetal, a ketal, a carbamate, a thiocyanate, an activated ester, an activated acid, a hydrazine, a hydrazone, and combinations thereof.

11. The method of claim 9 wherein the functionalized carbene has the following formula:

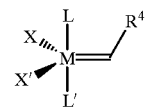

Formula II wherein M is Ru or Os, X and X' are each independently an anionic ligand, L and L' are each independently a neutral ligand, and $R^4$ is an organic group that includes a latent reactive group selected from the group consisting of an azide, an epoxide, a cyano group, an acetal, a ketal, a carbamate, a thiocyanate, an activated ester, an activated acid, a hydrazine, a hydrazone, and combinations thereof.

12. The method of claim 7 wherein the functionalized carbene catalyst comprises a nonreactive functional group.

13. The method of claim 12 wherein the functionalized carbene is represented by $M=CR^4R^5$, wherein $R^4$ is an organic group that includes a nonreactive functional group, $R^5$ is H or an organic group, and M represents ruthenium or osmium in a ligand sphere.

14. The method of claim 13 wherein $R^4$ is an organic group that includes a nonreactive functional group selected from the group consisting of natural products or analogs thereof, metal chelators, metals, fluorescent probes, solid supports, metal surfaces, and combinations thereof.

15. The method of claim 14 wherein the functionalized carbene has the following formula:

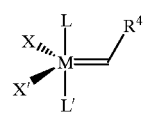

Formula II wherein M is Ru or Os, X and X' are each independently an anionic ligand, L and L' are each independently a neutral ligand, and $R^4$ is an organic group that includes a nonreactive functional group selected from the group consisting of natural products or analogs thereof, metal chelators, metals, fluorescent probes, solid supports, metal surfaces, and combinations thereof.

16. The method of claim 7 wherein the polymer is a monotelechelic polymer.

17. A method of preparing a bitelechelic polymer, the method comprising the steps of:
polymerizing at least one monomer comprising at least one group that can be polymerized through ring-opening metathesis polymerization in the presence of at least one functionalized ruthenium or osmium carbene catalyst to form a functionalized polymer template; and
combining the functionalized polymer template with at least one functionalized capping agent containing an electron donating group under conditions effective to react the functionalized polymer template with the capping agent to form a bitelechelic polymer.

18. The method of claim 17 wherein the functionalized capping agent comprises a latent reactive group for subsequent reaction with a functionalizing reagent.

19. The method of claim 18 wherein the functionalized capping agent has the following formula:

Formula III

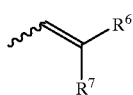

wherein D is an electron donating group and $R^6$ is an organic group that includes a latent reactive group selected from the group consisting of an azide, a nitro group, a disulfide, a hydrazine, a hydrazide, a hydroxylamine, an aldehyde, a ketone, an epoxide, a cyano group, an acetal, a ketal, a carbamate, a thiocyanate, an activated ester, an activated acid, and combinations thereof, and $R^7$ is H or an organic group.

20. The method of claim 17 wherein the functionalized capping agent comprises a nonreactive functional group.

21. The method of claim 20 wherein the functionalized capping agent has the following formula:

Formula III

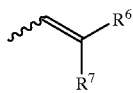

wherein D is an electron donating group and $R^6$ is an organic group that includes a nonreactive functional group selected from the group consisting of natural products or analogs thereof, metal chelators, metals, fluorescent probes, solid supports, metal surfaces, and combinations thereof, and $R^7$ is H or an organic group.

22. The method of claim 17 wherein the functionalized carbene catalyst comprises a latent reactive group for subsequent reaction with a functionalizing reagent.

23. The method of claim 22 wherein the functionalized carbene is represented by $M=CR^4R^5$, wherein $R^4$ is an organic group that includes a latent reactive group, $R^5$ is H or an organic group, and M represents ruthenium or osmium in a ligand sphere.

24. The method of claim 23 wherein $R^4$ is an organic group that includes a latent reactive group selected from the group consisting of an azide, an epoxide, a cyano group, an acetal, a ketal, a carbamate, a thiocyanate, an activated ester, an activated acid, a hydrazine, a hydrazone, and combinations thereof.

25. The method of claim 24 wherein the functionalized carbene has the following formula:

Formula II

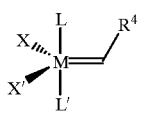

wherein M is Ru or Os, X and X' are each independently an anionic ligand, L and L' are each independently a neutral ligand, and $R^4$ is an organic group that includes a latent reactive group selected from the group consisting of an azide, an epoxide, a cyano group, an acetal, a ketal, a carbamate, a thiocyanate, an activated ester, an activated acid, a hydrazine, a hydrazone, and combinations thereof.

26. The method of claim 17 wherein the functionalized carbene catalyst comprises a nonreactive functional group.

27. The method of claim 26 wherein the functionalized carbene is represented by $M=CR^4R^5$, wherein $R^4$ is an organic group that includes a nonreactive functional group, $R^5$ is H or an organic group, and M represents ruthenium or osmium in a ligand sphere.

28. The method of claim 27 wherein $R^4$ is an organic group that includes a nonreactive functional group selected from the group consisting of natural products or analogs thereof, metal chelators, metals, fluorescent probes, solid supports, metal surfaces, and combinations thereof.

29. The method of claim 28 wherein the functionalized carbene has the following formula:

Formula II

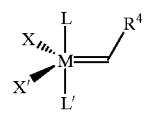

wherein M is Ru or Os, X and X' are each independently an anionic ligand, L and L' are each independently a neutral ligand, and $R^4$ is an organic group that includes a nonreactive functional group selected from the group consisting of natural products or analogs thereof, metal chelators, metals, fluorescent probes, solid supports, metal surfaces, and combinations thereof.

30. The method of claim 1 wherein the monomer is a cyclic mono-olefin.

31. The method of claim 1 wherein the monomer further comprises a latent reactive group.

32. The method of claim 1 wherein the capping agent is an olefin with the electron donating group bonded to an olefinic carbon.

33. The method of claim 1 wherein the capping agent is an alkyl vinyl ether linked to a protected carboxylic acid derivative via an ethylene glycol chain.

34. The method of claim 2 further comprising the step of reacting the terminally functionalized polymer, which comprises a latent reactive group from reaction with the capping agent, with a functionalizing reagent.

35. The method of claim 34 wherein reaction with the functionalizing reagent introduces functionality at a terminus of the polymer to allow for coupling of two polymers together, or coupling to a solid support.

36. The method of claim 34 wherein reaction with the functionalizing reagent introduces a functional group selected from the group consisting of a fluorescent probe, a protein, a metal, and a metal chelator at a terminus of the polymer.

37. The method of claim 34 wherein reaction with the functionalizing reagent introduces a functional group that is a reporter group at a terminus of the polymer.

38. The method of claim 37 wherein the reporter group is selected from a fluorescent group, a chemiluminescent group, an enzyme, an antibody, biotin, and a radioactive group.

39. The method of claim 7 wherein the monomer is a cyclic mono-olefin.

40. The method of claim 7 wherein the capping agent is an olefin with the electron donating group bonded to an olefinic carbon.

41. The method of claim 8 wherein the latent reactive group is an electrophile or a nucleophile.

42. The method of claim 8 further comprising the step of reacting the terminally functionalized polymer, which comprises a latent reactive group from the functionalized carbene catalyst with a functionalizing reagent to react with the latent reactive group.

43. The method of claim 12 wherein the nonreactive functional group is a reporter group.

44. The method of claim 43 wherein the reporter group is selected from a fluorescent group, a chemiluminescent group, an enzyme, an antibody, biotin, and a radioactive group.

45. The method of claim 17 wherein the monomer is a cyclic mono-olefin.

46. The method of claim 17 wherein the capping agent is an olefin with the electron donating group bonded to an olefinic carbon.

47. The method of claim 18 further comprising the step of reacting the terminally functionalized polymer, which comprises a latent reactive group from the capping agent, with a functionalizing reagent.

48. The method of claim 20 wherein the nonfunctional group is a reporter group.

* * * * *

UNITED STATES PATENT AND TRADEMARK OFFICE
CERTIFICATE OF CORRECTION

PATENT NO.   : 6,291,616 B1
DATED        : September 18, 2001
INVENTOR(S)  : Kiessling et al.

It is certified that error appears in the above-identified patent and that said Letters Patent is hereby corrected as shown below:

Title page,
Item [56], References Cited, OTHER PUBLICATIONS, please replace "10582" with -- 10575-10582 --.
Please replace "$_{exo}$" with -- exo --.

Column 3,
Line 61, please replace "2,2',2'" with -- 2,2'2," --.

Column 5,
Lines 17 and 18, please delete "incorporated from US patent application Ser. No. 09/335,430, filed Jun. 17, 1999:".

Column 12,
Line 14, please replace "$C_{1-c100}$" with -- $C_1$-$C_{100}$ --.

Column 15,
Lines 46-47, please enter a hard return after "61.7." to create a new paragraph beginning with -- 10-Phenyl-3, 6,9-trioxadecanoic acid --.

Column 29,
Lines 3 through 5, please replace the chemical structure with:

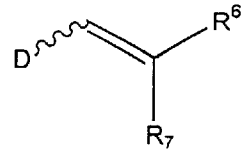

Lines 22 through 25, please replace the chemical structure with:

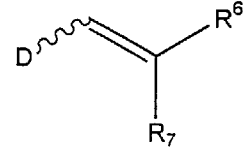

Signed and Sealed this

Tenth Day of September, 2002

Attest:

JAMES E. ROGAN
Attesting Officer         Director of the United States Patent and Trademark Office